United States Patent
Zhou et al.

(10) Patent No.: US 10,981,993 B2
(45) Date of Patent: Apr. 20, 2021

(54) ANTI-PD-1 MONOCLONAL ANTIBODY AND OBTAINING METHOD THEREFOR

(71) Applicants: BEIJING DONGFANG BIOTECH CO., LTD., Beijing (CN); BEIJING JINGYITAIXIANG TECHNOLOGY DEVELOPMENT CO., LTD., Beijing (CN)

(72) Inventors: Haiping Zhou, Beijing (CN); Xiaomin Li, Beijing (CN); Junjie Zhou, Beijing (CN); Shuang Pei, Beijing (CN); Yanlu Zan, Beijing (CN); Yi Bai, Beijing (CN); Xianhong Bai, Beijing (CN)

(73) Assignees: BEIJING DONGFANG BIOTECH CO., LTD., Beijing (CN); BEIJING JINGYITAIXIANG TECHNOLOGY DEVELOPMENT CO., LTD., Beijing (CN)

( * ) Notice: Subject to any disclaimer, the term of this patent is extended or adjusted under 35 U.S.C. 154(b) by 190 days.

(21) Appl. No.: 16/251,473

(22) Filed: Jan. 18, 2019

(65) Prior Publication Data
US 2019/0144541 A1 May 16, 2019

Related U.S. Application Data

(63) Continuation-in-part of application No. 15/501,812, filed on Feb. 3, 2017, now abandoned.

(51) Int. Cl.
C07K 16/28 (2006.01)
A61K 39/395 (2006.01)
A61K 47/68 (2017.01)

(52) U.S. Cl.
CPC ...... *C07K 16/2818* (2013.01); *A61K 47/6803* (2017.08); *A61K 47/6849* (2017.08); *C07K 2317/21* (2013.01); *C07K 2317/31* (2013.01); *C07K 2317/565* (2013.01); *C07K 2317/622* (2013.01); *C07K 2317/76* (2013.01); *C07K 2317/92* (2013.01)

(58) Field of Classification Search
CPC combination set(s) only.
See application file for complete search history.

(56) References Cited

FOREIGN PATENT DOCUMENTS

WO   WO-2019062642 A1 * 4/2019 ........... A61K 39/395

* cited by examiner

*Primary Examiner* — Hong Sang
(74) *Attorney, Agent, or Firm* — CBM Patent Consulting, LLC

(57) ABSTRACT

The invention provides human monoclonal antibodies that specifically bind to PD-1 with high affinity. The anti-PD-1 monoclonal antibodies were screened from a synthetic antibody library, and affinity maturation was performed. The synthetic antibody libraries used to select for the high affinity anti-PD-1 monoclonal antibodies were made by replacing the light chain CDR1, CDR2 and CDR3 and heavy chain CDR1, CDR 2 and CDR 3 of phage libraries from the preliminary screening, and the high affinity anti-PD-1 monoclonal antibodies were selected. The human anti-PD-1 monoclonal antibodies have high affinity and inhibit the binding of PD-1 to its ligand PD-L1. The antibodies can be used for treating tumor, inflammation and autoimmune diseases.

4 Claims, 8 Drawing Sheets

Specification includes a Sequence Listing.

ANTI-PD-1 MONOCLONAL ANTIBODY AND OBTAINING METHOD THEREFOR

This application is a continuation in part of U.S. Ser. No. 15/501,812 filed on 3 Feb. 2017 claims priority to the U.S. national phase of International Application No. PCT/CN2015/091842 Filed on 13 Oct. 2015 which designated the U.S. and claims priority to Chinese Application No. CN201510312910.8 filed on 9 Jun. 2015, the entire contents of each of which are hereby incorporated by reference.

TECHNICAL FIELD OF THE INVENTION

The present invention relates to an antibody, obtaining method and application thereof. Specifically, the present invention relates to human anti-PD-1 monoclonal antibodies, polynucleotide sequences or combination, vectors, host cells and drugs, obtaining method and application thereof.

BACKGROUND OF THE INVENTION

Programmed Cell Death 1 (PD-1) and its ligand (PD-L1, also termed as CD274 or B7H1) are members of the CD28/B7 super-family that can mediate negative co-stimulatory signal. PD-1/PD-L1 signaling pathway can inhibit T and B cell function, and T cell proliferation, while reduce the secretion of cytokines IL-2, IL-10 and IFN-γ. It plays an important role in immune regulation, and has a major significance in the study of tumor immunity, autoimmunity, transplantation immunology, asthma, viral infections and other diseases.

Many large international pharmaceutical companies have been studying on monoclonal antibody drugs PD-1 or PD-L1, wherein the Bristol-Myers Squibb Company owned PD-1 inhibitor Opdivo (Nivolumab) was approved in Japan in July, 2014; Merck PD-1 inhibitor was approved by the FDA in September, 2014. The first indication of these two drugs is melanoma. With the advance of each company's clinical programs, indications will expand to lung cancer, breast cancer, cancer of the blood and other fields.

Accordingly, it is encouraging to make more efforts on developing new human anti-PD-1 monoclonal antibodies, and applying the antibodies in clinical practice and so on.

SUMMARY OF THE INVENTION

The present invention aims at providing human anti-PD-1 monoclonal antibodies, obtaining method and application thereof.

A human anti-PD-1 monoclonal antibody DFPD1-1 is first selected from the synthetic antibody library. The DFPD1-1 was analyzed and then small-capacity mutant library was designed by computer-aided design based on this antibody. Then a mutant library of the light chain CDR1, CDR2 and CDR3 was created, higher affinity of monoclonal antibodies, DFPD1-3 and DFPD1-7, were selected by screening. A mutant library of its heavy chain CDR1, CDR 2 and CDR 3 was created based on DFPD1-1, DFPD1-3 and PFPD1-7 higher affinity anti-PD-1 monoclonal antibodies were selected.

In order to achieve the above purpose, the present invention provides an obtaining method of anti-PD-1 monoclonal antibodies, which includes:

(1): The biopanning of anti-PD-1 single-chain antibody. A high affinity antibody DFPD1-1 was obtained from a fully-synthetic ScFv phage library through three rounds of enriching and screening. Its heavy chain is DFPD1-H1 (SEQ ID NO.1), and its light chain is DFPD1-L1 (SEQ ID NO.5).

Antibody clone DFPD1-1 has one light chain whose full amino acid sequence shown as SEQ ID NO. 54, which is encoded by a nuclei acid sequence shown as SEQ ID NO. 65, and one heavy chain whose full amino acid sequence shown as SEQ ID NO. 53, which is encoded by a nuclei acid sequence shown as SEQ ID NO. 64. The SEQ ID NO. 54 consists of SEQ ID NO.5 and SEQ ID NO.15, and the SEQ ID NO. 53 consists of SEQ ID NO.1 and SEQ ID NO.16.

The SEQ ID NO.15, which is encoded by a nuclei acid sequence shown as SEQ ID NO. 17, is the amino acid sequence for the constant region of light chain of human antibody. The SEQ ID NO.16, which is encoded by a nuclei acid sequence shown as SEQ ID NO. 14, is the amino acid sequence for the constant region of heavy chain of human antibody.

(2): Based on DFPD1-1, a mutant library of light chain CDR1, CDR2 and CDR3 was designed by analyzing DFPD1-1 tertiary structure with computer-aided design. A mutant library of light chain CDR1,CDR2 and CDR3 were created, bio-panned screened. By identifying the positive clones and comparing the affinity of single-chain antibodies on the phage level, six different antibody light chains (DFPD1-2, DFPD1-3, DFPD1-4, DFPD1-5, DFPD1-6 and DFPD1-7) were obtained, and their corresponding light chain sequences were DFPD1-L2 (SEQ ID NO.6), DFPD-L3 (SEQ ID NO.7), DFPD1-L4 (SEQ ID NO.8), DFPD1-L5 (SEQ ID NO.9), DFPD1-L6 (SEQ ID NO.10), DFPD1-L7 (SEQ ID NO.11).

Antibody clone DFPD1-2 has one light chain whose full amino acid sequence shown as SEQ ID NO. 55, which is encoded by a nuclei acid sequence shown as SEQ ID NO. 66, and one heavy chain whose full amino acid sequence shown as SEQ ID NO. 53, which is encoded by a nuclei acid sequence shown as SEQ ID NO. 64. The SEQ ID NO. 55 consists of SEQ ID NO.6 and SEQ ID NO.15, and the SEQ ID NO. 53 consists of SEQ ID NO.1 and SEQ ID NO.16.

Antibody clone DFPD1-3 has one light chain whose full amino acid sequence shown as SEQ ID NO. 56, which is encoded by a nuclei acid sequence shown as SEQ ID NO. 67, and one heavy chain whose full amino acid sequence shown as SEQ ID NO. 53, which is encoded by a nuclei acid sequence shown as SEQ ID NO. 64. The SEQ ID NO. 56 consists of SEQ ID NO.7 and SEQ ID NO.15, and the SEQ ID NO. 53 consists of SEQ ID NO.1 and SEQ ID NO.16.

Antibody clone DFPD1-4 has one light chain whose full amino acid sequence shown as SEQ ID NO. 57, which is encoded by a nuclei acid sequence shown as SEQ ID NO. 68, and one heavy chain whose full amino acid sequence shown as SEQ ID NO. 53 which is encoded by a nuclei acid sequence shown as SEQ ID NO. 64. The SEQ ID NO. 57 consists of SEQ ID NO.8 and SEQ ID NO.15, and the SEQ ID NO. 53 consists of SEQ ID NO.1 and SEQ ID NO.16.

Antibody clone DFPD1-5 has one light chain whose full amino acid sequence shown as SEQ ID NO. 58, which is encoded by a nuclei acid sequence shown as SEQ ID NO. 69, and one heavy chain whose full amino acid sequence shown as SEQ ID NO. 53 which is encoded by a nuclei acid sequence shown as SEQ ID NO. 64. The SEQ ID NO. 58 consists of SEQ ID NO.9 and SEQ ID NO.15, and the SEQ ID NO. 53 consists of SEQ ID NO.1 and SEQ ID NO.16.

Antibody clone DFPD1-6 has one light chain whose full amino acid sequence shown as SEQ ID NO. 59, which is encoded by a nuclei acid sequence shown as SEQ ID NO. 70, and one heavy chain whose full amino acid sequence shown as SEQ ID NO. 53, which is encoded by a nuclei acid sequence shown as SEQ ID NO. 64. The SEQ ID NO. 59 consists of SEQ ID NO.10 and SEQ ID NO.15, and the SEQ ID NO. 53 consists of SEQ ID NO.1 and SEQ ID NO.16.

Antibody clone DFPD1-7 has one light chain whose full amino acid sequence shown as SEQ ID NO. 60, which is encoded by a nuclei acid sequence shown as SEQ ID NO. 71, and one heavy chain whose full amino acid sequence shown as SEQ ID NO. 53 which is encoded by a nuclei acid sequence shown as SEQ ID NO. 64. The SEQ ID NO. 60 consists of SEQ ID NO.11 and SEQ ID NO.15, and the SEQ ID NO. 53 consists of SEQ ID NO.1 and SEQ ID NO.16.

(3): Based on two higher affinity clones DFPD1-3 and DFPD1-7, a mutant library of heavy chain CDR1, CDR2 and CDR3 was designed, bio-panned and screened, five different single-chain antibodies (clone No: DFPD1-9, DFPD1-10, DFPD1-11, DFPD1-12 and DFPD1-13) were selected. Wherein, the light chain variable region sequence of DFPD1-9, DFPD1-11 and DFPD1-12 is DFPD1-L3, and the light chain variable region sequence of DFPD1-10 and DFPD1-13 is DFPD1-L7. The heavy chain variable region sequence of DFPD1-9 and DFPD1-10 is DFPD1-H2 (SEQ ID NO.2), the heavy chain variable region sequence of DFPD1-11 and DFPD1-13 is DFPD1-H3 (SEQ ID NO.3), the heavy chain variable region sequence of DFPD1-12 is DFPD1-H4 (SEQ ID NO.4).

Antibody clone DFPD1-9 has one light chain whose full amino acid sequence shown as SEQ ID NO. 56, which is encoded by a nuclei acid sequence shown as SEQ ID NO. 67, and one heavy chain whose full amino acid sequence shown as SEQ ID NO. 61 which is encoded by a nuclei acid sequence shown as SEQ ID NO. 72. The SEQ ID NO. 56 consists of SEQ ID NO. 7 and SEQ ID NO.15, and the SEQ ID NO. 61 consists of SEQ ID NO.2 and SEQ ID NO.16.

Antibody clone DFPD1-10 has one light chain whose full amino acid sequence shown as SEQ ID NO. 60, which is encoded by a nuclei acid sequence shown as SEQ ID NO. 71, and one heavy chain whose full amino acid sequence shown as SEQ ID NO. 61 which is encoded by a nuclei acid sequence shown as SEQ ID NO. 72. The SEQ ID NO. 60 consists of SEQ ID NO.11 and SEQ ID NO.15, and the SEQ ID NO. 61 consists of SEQ ID NO.2 and SEQ ID NO.16.

Antibody clone DFPD1-11 has one light chain whose full amino acid sequence shown as SEQ ID NO. 56, which is encoded by a nuclei acid sequence shown as SEQ ID NO. 67, and one heavy chain whose full amino acid sequence shown as SEQ ID NO. 62, which is encoded by a nuclei acid sequence shown as SEQ ID NO. 73. The SEQ ID NO. 56 consists of SEQ ID NO. 7 and SEQ ID NO.15, and the SEQ ID NO. 62 consists of SEQ ID NO. 3 and SEQ ID NO.16.

Antibody clone DFPD1-12 has one light chain whose full amino acid sequence shown as SEQ ID NO. 56, which is encoded by a nuclei acid sequence shown as SEQ ID NO. 67, and one heavy chain whose full amino acid sequence shown as SEQ ID NO. 63 which is encoded by a nuclei acid sequence shown as SEQ ID NO. 74. The SEQ ID NO. 56 consists of SEQ ID NO. 7 and SEQ ID NO.15, and the SEQ ID NO. 63 consists of SEQ ID NO. 4 and SEQ ID NO.16.

Antibody clone DFPD1-13 has one light chain whose full amino acid sequence shown as SEQ ID NO. 60, which is encoded by a nuclei acid sequence shown as SEQ ID NO. 71, and one heavy chain whose full amino acid sequence shown as SEQ ID NO. 62 which is encoded by a nuclei acid sequence shown as SEQ ID NO. 73. The SEQ ID NO. 60 consists of SEQ ID NO.11 and SEQ ID NO.15, and the SEQ ID NO. 62 consists of SEQ ID NO. 3 and SEQ ID NO.16.

(4): Genes which encode the variable region of the heavy chain and the light chain of the monoclonal antibodies were described in step 3. The corresponding constant region genes were cloned into the eukaryotic expression vector and transfected into host cells. The monoclonal antibodies were purified, then affinity and other biological functions of whole monoclonal antibodies were compared.

The anti-PD-1 monoclonal antibodies were obtained by the above method, including the light chain and the heavy chain, the light chain CDR1, CDR2 and CDR3 are represented by LCDR1, LCDR2 and LCDR3, LCDR1 contains RASQNIHSYLD (SEQ ID NO.18), RASQNVSNWLD (SEQ ID NO.19), RASQSIHNYLD(SEQ ID NO.20), RASQDINNWLD(SEQ ID NO.21), RASQDVRNYLD (SEQ ID NO.22), RASQGINSWLD(SEQ ID NO.23) or RASQSVSNYLD(SEQ ID NO.24), LCDR2 contains EASTRAS(SEQ ID NO.25), DASNRAT (SEQ ID NO.26), NASTRAT(SEQ ID NO.27), DASTLAT(SEQ ID NO.28), GASTRAT(SEQ ID NO.29) or DASTRAT(SEQ ID NO.30), LCDR3 contains QQALKLPIT(SEQ ID NO.31), QQSRHIPLT(SEQ ID NO.32), QQELHLPLT(SEQ ID NO.33), QQNVNLPLT(SEQ ID NO.34), QQDIDLPLT (SEQ ID NO.35), QQSYRLPLT(SEQ ID NO.36) or QQNMQLPLT(SEQ ID NO.37).

Wherein, the amino acid sequence of the light chain variable region is SEQ ID NO.5, SEQ ID NO.6, SEQ ID NO.7, SEQ ID NO.8, SEQ ID NO.9, SEQ ID NO.10 or SEQ ID NO.11.

The anti-PD-1 monoclonal antibodies were obtained by the above method, including the light chain and heavy chain, the heavy chain CDR1, CDR2 and CDR3 is represented by HCDR1, HCDR2 and HCDR3, HCDR1 contains SNNGMH (SEQ ID NO.38) or SNYGMH (SEQ ID NO.39), HCDR2 contains VIWYDGSKK (SEQ ID NO.40), VIWYDSSRK (SEQ ID NO.41) or VIWYDSTKK (SEQ ID NO.42), HCDR3 contains TAVYYCATNNDYW (SEQ ID NO.43) or TAVYYCATNTDYW (SEQ ID NO.44).

Wherein, the amino acid sequence of the heavy chain variable region is SEQ ID NO.1, SEQ ID NO.2, SEQ ID NO.3 or SEQ ID NO.4.

This invention also provides antibodies, polypeptides or proteins which contain said light chain or heavy chain.

This invention also provides antibodies that contain said light chain or heavy chain. And said antibodies can block the binding of PD-1 to its ligands PD-L1, consequently inhibit the biological activity of PD-1.

This invention also provides polynucleotide sequences or combinations which encode said light chain or heavy chain.

This invention also provides recombinant DNA expression vectors which contain DNA sequences encoding the variable regions and/or the constant regions of the heavy chain and the light chain of the anti-PD-1 antibody.

This invention also provides host cells transfected with the said recombinant DNA expression vectors, while the host cell is selected from the group consisting of *E. coli* and other prokaryotic cells, yeasts and mammalian cells.

Preferably, the host cells are HEK293E cells, CHO cells or NS0 cells and so on.

This invention also provides whole antibodies, single domain antibodies, bi-specific antibodies, antibody-drug conjugates and/or chimeric antigen receptor T-cell immunotherapy which contain said sequences.

This invention also provides monoclonal antibodies, artificial vectors, a drug or combinations of drugs which contain the said light chain or heavy chain.

This invention also provides detection reagents or kits which contain the said light chain or heavy chain.

Wherein, the anti-PD-1 monoclonal antibody contains whole antibody and its fragments, the fragments include, but not limited to Fab, Fab', F (ab') 2, Fv or ScFv.

Wherein, the full-length antibodies are human monoclonal antibodies.

Wherein, the constant region of the heavy chain of anti-PD-1 monoclonal antibody is IgG1, IgG2, IgG3 or IgG4, the constant region of the light chain is $C_\kappa$ or $C_\lambda$.

Preferably, the constant region of the heavy chain is IgG4.

Preferably, the constant region of the light chain is $C_\kappa$.

The CDR is the abbreviation of complementary determining region, the ScFv is the abbreviation of single-chain fragment variable, the CAR-T is the abbreviation of chimeric antigen receptor T-cell immunotherapy, the Fab is the abbreviation of antigen binding fragment, the HEK293E cell is human embryonic kidney 293E cell, the CHO cell is china hamster ovary cell, the NS0 cell is NS0 mouse thymoma cell.

Compared with the prior art, the beneficial effects of the present invention can prevent and treat diseases by inhibiting the activity of PD-1, wherein the diseases are selected from the group consisting of cancer, infectious diseases or immune system disorders. Types of cancer include, but are not limited to lung cancer, kidney cancer, melanoma, breast cancer, liver cancer, head and neck cancer, skin cancer, squamous cell carcinoma, ovarian cancer, bone cancer, colorectal cancer, bladder cancer, stomach cancer, pancreatic cancer, prostate cancer, Hodgkin's lymphoma, follicular lymphoma, chronic or acute leukemia or solid tumors. Infectious diseases include, but not limited to HIV infection, hepatitis virus (type A, B and C) infection, herpes virus infection or influenza virus infection. Immune system disorders include, but not limited to lupus erythematosus, rheumatoid arthritis, ankylosing spondylitis, myasthenia gravis, multiple sclerosis, autoimmune hemolytic anemia, autoimmune hepatitis, scleroderma, poly-arteritis or Wegener's granulomatosis.

DETAILED DESCRIPTION OF EXEMPLARY EMBODIMENTS

Figure 1:
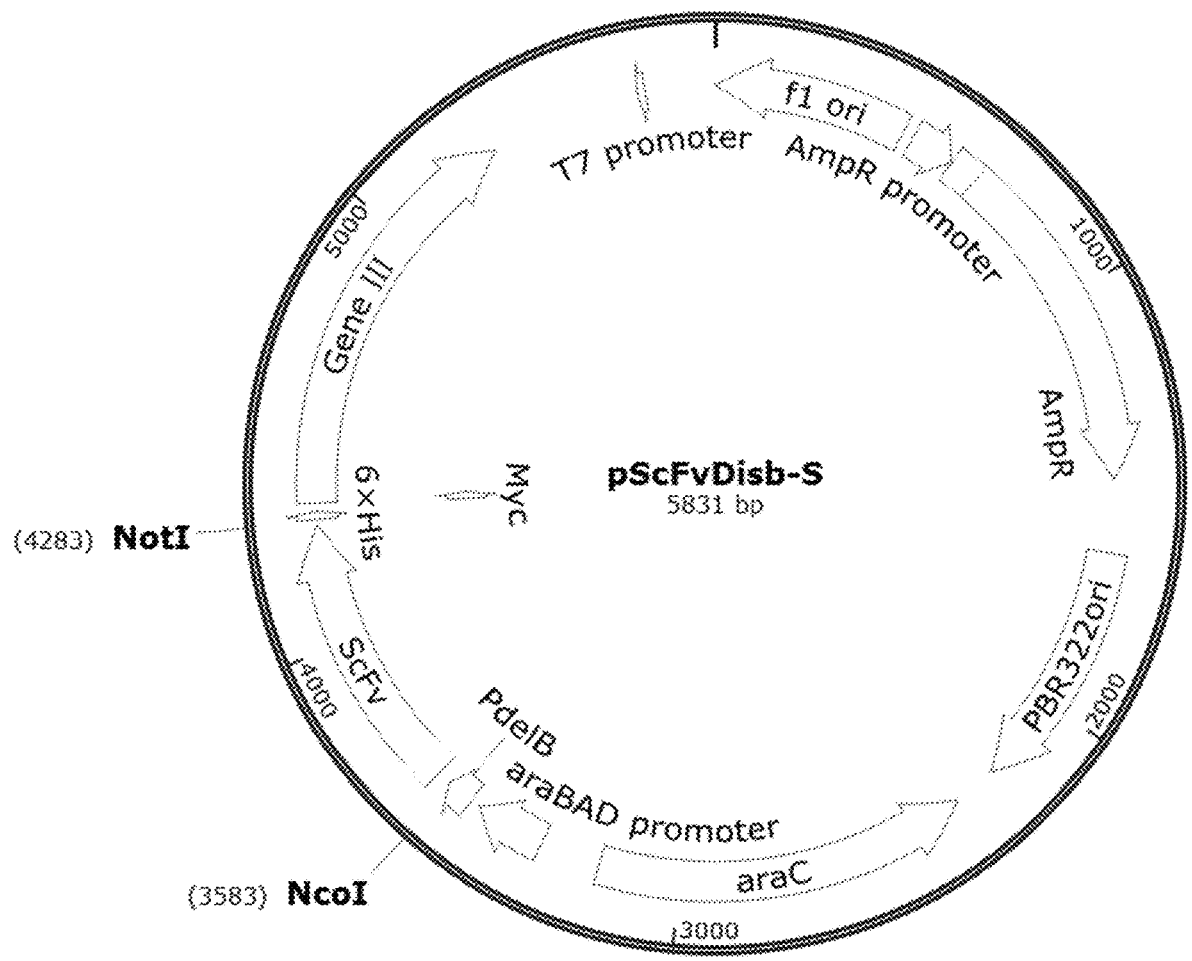
FIG. 1 shows the plasmid vector map of pScFvDisb-s.

The embodiment mode of this invention is described in the following examples. However, it should be noted that the embodiment is not limited to certain details of these examples.

The experimental methods described in the following examples are all common technologies unless otherwise specified; the reagents and biological described are all commercially available unless otherwise specified.

The present invention provides a monoclonal antibody, which specifically interacts with PD-1, the heavy chain variable region sequence is selected from the group consisting of SEQ ID NO.1, SEQ ID NO.2, SEQ ID NO.3 and SEQ ID NO. 4, the light chain variable region sequence is selected from the group consisting of SEQ ID NO.5, SEQ ID NO.6, SEQ ID NO.7, SEQ ID NO.8, SEQ ID NO.9, SEQ ID NO.10 and SEQ ID NO.11.

Preferably, the heavy chain variable region sequence is SEQ ID NO.2, SEQ ID NO.3 or SEQ ID NO. 4, the light chain variable region sequence is SEQ ID NO.7 or SEQ ID NO.11.

Through screening the phage library of the light chain, the amino acid sequence of the LCDR1, LCDR2 or LCDR3 of the light chain or its functional fragment of the monoclonal antibody are selected from the following group (as shown in Table 1).

TABLE 1

The Amino Acid Sequence Of Each CDR In The Light Chain

| No. | LCDR1 | LCDR2 | LCDR3 |
|---|---|---|---|
| A | RASQNIHSYLD (SEQ ID NO. 18) | EASTRAS (SEQ ID NO. 25) | QQALKLPIT (SEQ ID NO. 31) |
| B | RASQNVSNWLD (SEQ ID NO. 19) | DASNRAT (SEQ ID NO. 26) | QQSRHIPLT (SEQ ID NO. 32) |

TABLE 1-continued

The Amino Acid Sequence Of Each CDR In The Light Chain

| No. | LCDR1 | LCDR2 | LCDR3 |
|---|---|---|---|
| C | RASQSIHNYLD (SEQ ID NO. 20) | NASTRAT (SEQ ID NO. 27) | QQELHLPLT (SEQ ID NO. 33) |
| D | RASQDINNWLD (SEQ ID NO. 21) | DASTLAT (SEQ ID NO. 28) | QQNVNLPLT (SEQ ID NO. 34) |
| E | RASQDVRNYLD (SEQ ID NO. 22) | GASTRAT (SEQ ID NO. 29) | QQDIDLPLT (SEQ ID NO. 35) |
| F | RASQGINSWLD (SEQ ID NO. 23) | DASTRAT (SEQ ID NO. 30) | QQSYRLPLT (SEQ ID NO. 36) |
| G | RASQSVSNYLD (SEQ ID NO. 24) | DASTRAT (SEQ ID NO. 30) | QQNMQLPLT (SEQ ID NO. 37) |

Through screening the phage library of the heavy chain, the CDR1, CDR2 or CDR3 of the heavy chain or its functional fragment of the monoclonal antibodies are represented by HCDR1, HCDR2 or HCDR3, HCDR1 contains SNNGMH(SEQ ID NO. 38) or SNYGMH(SEQ ID NO.39), HCDR2 contains VIWYDGSKK (SEQ ID NO. 40), VIWYDSSRK (SEQ ID NO. 41) or VIWYDSTKK (SEQ ID NO. 42), HCDR3 contains TAVYYCATNNDYW (SEQ ID NO. 43) or TAVYYCATNTDYW (SEQ ID NO. 44).

Preferably, through screening the phage library of the heavy chain, the heavy chain variable region of the monoclonal antibody specifically interacted with PD-1 contains HCDR1, HCDR2 and HCDR3 sequence, and the light chain variable region contains LCDR1, LCDR2 and LCDR3 sequence. Wherein, HCDR1 sequence of the heavy chain variable region contains SNNGMH(SEQ ID NO. 38) or SNYGMH(SEQ ID NO. 39), LCDR1 sequence of the light chain variable region contains RASQSIHNYLD (SEQ ID NO. 20) or RASQSVSNYLD(SEQ ID NO. 24), HCDR2 sequence of the heavy chain variable region contains VIWYDGSKK (SEQ ID NO. 40) or VIWYDSSRK (SEQ ID NO. 41), LCDR2 sequence of the light chain variable region contains NASTRAT (SEQ ID NO.27) or DASTRAT (SEQ ID NO. 30), HCDR3 sequence of the heavy chain variable region contains TAVYYCATNNDYW (SEQ ID NO. 43) or TAVYYCATNTDYW (SEQ ID NO. 44), LCDR3 sequence of the light chain variable region contains QQELHLPLT (SEQ ID NO. 33) or QQNMQLPLT(SEQ ID NO. 37).

In the present invention, the antibody, which specifically interacts with PD-1, is obtained from the synthetic ScFv phage library, the process for preparing the anti-PD-1 monoclonal antibodies including:

First of all, anti-PD-1 single-chain antibody library was bio-panned through three rounds of enriching and screening of the antibody library, and a high affinity antibody DFPD1-1 was obtained.

Secondly, a light chain CDR1, CDR2 or CDR3 mutant library was designed by computer aided design based on DFPD1-1. Six different light chain antibodies (DFPD1-2, DFPD1-3, DFPD1-4, DFPD1-5, DFPD1-6 or DFPD1-7) were identified as positive clones by bio-panning and comparing the affinities of the ScFvs on the level of phage.

Thirdly, a heavy chain CDR1, CDR2 and CDR3 mutant library was built on basis of two higher affinity strains of clones DFPD1-3 and DFPD1-7. Five different single-chain antibodies which are DFPD1-9, DFPD1-10, DFPD1-11, DFPD1-12, DFPD1-13 were selected by bio-panning and comparing the affinities of the ScFvs on the level of phage.

Finally, the variable region genes of the heavy chain and the light chain of the monoclonal antibody which are described above and their corresponding constant region genes were cloned into the eukaryotic expression vector and transfected into the host cells, obtained the monoclonal antibody, and then compared their affinity and other biological functions.

Example 1

The Biopanning of Anti-PD-1 Single-Chain Antibody Library pComb3 vector (Purchased from Biovector Science Lab, Inc.) was modified by a series of cloning technology for constructing and expressing of a single-chain antibody phage library. The modified vector is named as pScFvDisb-s shown in FIG. 1 and was used to make a fully-synthetic phage antibody library.

The immune tubes were coated with the antigen PD-1-His, the amount of antigen-coated is 5 µg/500 µL/tube at 4° C. overnight. The 4% skim milk/PBST was used to block the immune tubes and the full synthetic phage antibody library at room temperature for one hour. The blocked phage antibody library was added into the immune tubes for Ab-Ag interactions at room temperature for one hour, the amount of phage inputs was about $10^9$-$10^{12}$. PBST-PBS was used to wash the unbound phages, 0.1M Glycine-HCl (pH 2.2) was used to elute, 1.5M Tris-HCl (pH8.8) was used to neutralize the eluted phage antibody solution to about pH7.0.

The above neutralized phages infected 10 mL TG1 bacteria were grown to the logarithmic period, and set for 30 minutes at in 37° C. incubator. A partial of the bacteria culture was used for gradient diluting, coated on a 2×YT agar plate to calculate the amount of phage outputs. The remaining bacteria culture was centrifuged, then the supernatant was discarded. The thallus precipitation was suspended in a few of liquid culture media which was used to coat on a large 2×YT agar plate for the next round of screening.

The thallus was scraped from the large plate, inoculated to 2×YT liquid culture media, adding M13K07 for the helper phage super-infection after shaking to logarithmic period, culturing at 28° C. overnight to amplify the phages, PEG/NaCl is used to settle and purify the phage for the next round of screening. Three rounds of enrichment and screening the phage library are carried out in total.

Example 2

The Screening of Positive Clones for the Anti-PD-1 Phage Single-Chain Antibody

After three rounds of screening, the monoclonal bacterial colonies were selected to inoculate in a 96-well deep-well plates contained 2×YT liquid culture medium, and were cultured at 37° C. at 220 rpm to logarithmic growth period, then about $10^{10}$ helper phage M13K07 were added into each well for infection for 30 minutes at 37° C. Then the culture was centrifuged at 4000 rpm for 15 minutes, the supernatant was discarded, the thallus was suspended with 2×YT liquid culture medium. After culturing at 220 rpm 28° C. overnight, the culture was centrifuged at 4000 rpm for 15 minutes at 4° C., the phage supernatant was taken out for ELISA. The higher affinity single-chain antibody, DFPD1-1, was obtained by screening, the heavy chain variable region was named as DFPD1-H1 that has an amino acid sequence as shown in SEQ ID NO. 1, the light chain variable region was named DFPD1-L1 that has an amino acid sequence as shown in SEQ ID NO. 5.

Example 3

The Affinity Maturation Test In Vitro of the Anti-PD-1 Single-Chain Antibody DFPD1-1

1. The Construction of the Mutant Library for DFPD1-1 Light Chain CDR1,CDR2 and CDR3

Figure 2:
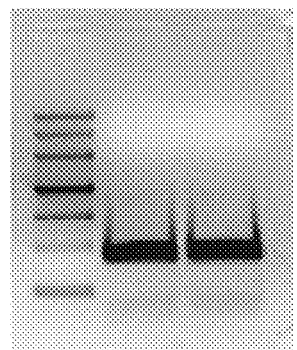
FIG. 2 shows the electrophoresis atlas of the PCR product of the heavy chain and the linker region by using DFPD1-1 as the template in building the mutant light chain variable region library.
Figure 3:
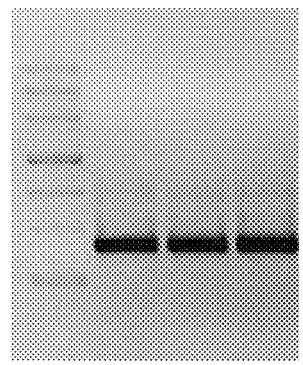
FIG. 3 shows the electrophoresis atlas of the PCR product obtained by using the synthetic mutant light chain library as template in building the mutant light chain variable region library.

The primers PVLF1 and PVLR1 were designed, using a DNA having a nucleic acid sequence shown as SEQ ID NO. 12 as a template, the light chain gene library (as shown in FIG. 3) were amplified by PCR; the primers PVHF1 and PVHR1, plasmid DFPD1-1 as the template were used to amplify its heavy chain and its linker ((as shown in FIG. 2). Reaction conditions: 95° C. for 30 second, 1 cycle, 95° C. for 15 seconds, 60° C. for 10 seconds, 72° C. for 30 seconds, 3 cycles, 95° C. for 15 seconds, 72° C. for 40 seconds, 25 cycles, 72° C. for 5 minutes, storing at 4° C. The PCR products were recovered with a universal recovery kit.

The sequences of primers as following:

(SEQ ID NO. 45)
PVLF1: 5'-GATATCCAGATGACCCAGAGC -3'

(SEQ ID NO. 46)
PVLR1: 5'- CTAAGCGGCCGCTTTGATCTCCACTTTGGTGC-3'

(SEQ ID NO. 47)
PVHF1: 5'-CATACCATGGCCCAGGTGCAGCTGGTGGAGTCTG-3'

(SEQ ID NO. 48)
PVHR1: 5'-GCTCTGGGTCATCTGGATATCGGATCCACCACC-3'

Figure 4:
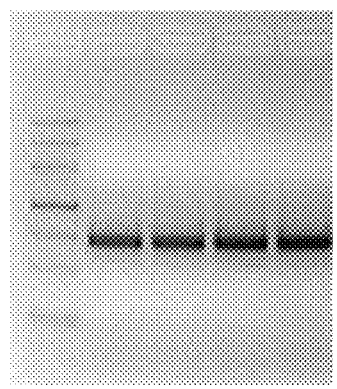
FIG. 4 shows the electrophoresis atlas of the PCR product in building the mutant light chain variable region library VLCDR123M-DFPD1-1.

The light chain mutation variable region library of DFPD1-1 was obtained by overlap PCR via amplifying two PCR products mentioned above. Reaction conditions: 95° C. for 30 seconds, 1 cycle, 95° C. for 15 seconds, 72° C. for 30 seconds, 4 cycle (added the primers PVHF1 and PVLR1), 95° C. for 15 seconds, 72° C. for 40 seconds, 25 cycles, 72° C. for 5 minutes, store at 4° C. The PCR products were recovered with universal recovery kit, the corresponding PCR product is named as VLCDR123M-DFPD1-1 (as shown in FIG. 4).

Figure 5:
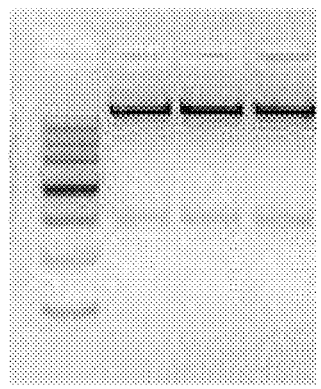
FIG. 5 shows the electrophoresis atlas of the double digested product of plasmid pScFvDisb-s in building the mutant light chain variable region library. and heavy chain variable region library by NcoI-HF and NotI.

The plasmid pScFvDisb-s and VLCDR123M-DFPD1-1 were digested with Nco I-HF and NotI, and the enzyme-digested products were run on 0.8% agarose gel electrophoresis (as shown in FIG. 5). After gel extraction, DNA was purified using a commercial available DNA purification kit. The purified digested VLCDR123M-DFPD1-1 and pScFvDisb-s was ligated at a molar ratio of 4:1 with T4 DNA Ligase for 4 hours at 16° C. The ligation product was transformed into TG1 competent cells by the electroporation. After recovering cells for one hour at 37° C. in SOC medium, a partial of the bacteria was plated on a culture dish to estimate the capacity of library. The remaining bacteria culture was centrifuged at room temperature at 4000 rpm for 15 minutes and the supernatant was removed. The precipitation was plated on 2×YT agar large plate, and cultured at 37° C. overnight.

The capacity of the antibody library is about $10^8$. Twenty clones were picked from the antibody library randomly for sequencing, the sequences showed 95% accuracy, and the capacity of the antibody library is of high diversity.

Figure 6:
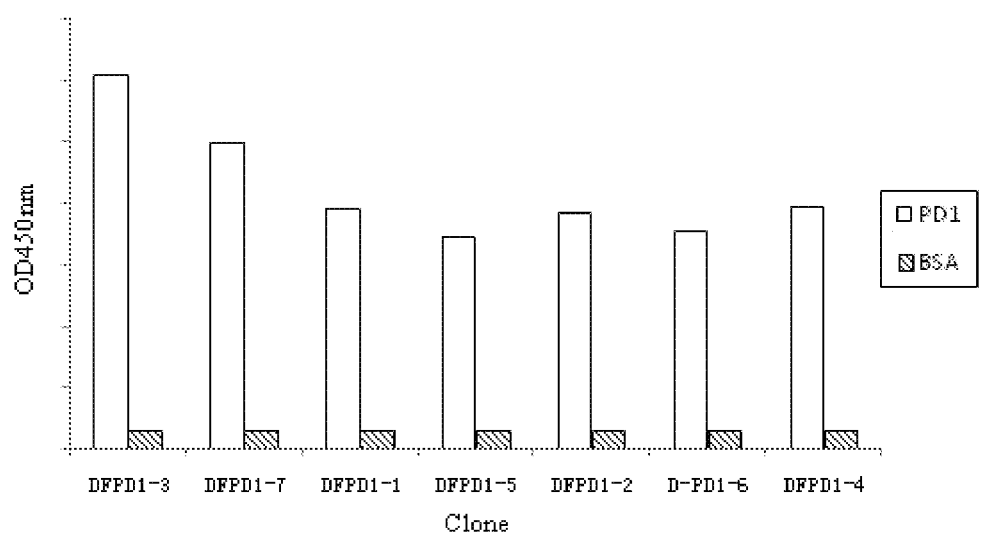
FIG. 6 shows relative affinity identification of the phage-Abs selected from the mutant light chain variable region library by monoclonal phage-ELISA.

2. The Bio-Panning of the Phage Antibody Library and Screening of Positive Clones The screening is in accordance with the method of the example 1, all clones which have high affinity were sequenced, then six different clones were obtained and named DFPD1-2, DFPD1-3, DFPD1-4, DFPD1-5, DFPD1-6 and DFPD1-7, respectively, the corresponding light chain variable region is named DFPD1-L2, DFPD1-L3, DFPD1-L4, DFPD1-L5, DFPD1-L6 and DFPD1-L7, the corresponding amino acid sequence is as shown in SEQ ID NO. 6, SEQ ID NO. 7, SEQ ID NO. 8, SEQ ID NO. 9, SEQ ID NO. 10 and SEQ ID NO. 11, respectively. The relative affinity of the monoclonal phage was determined with ELISA as shown in FIG. 6, wherein, the DFPD1-1 comprising a light chain having amino acid sequence shown as SEQ ID NO. 54 and a heavy chain having amino acid sequence shown as SEQ ID NO. 53, the DFPD1-2 comprising a light chain having amino acid sequence shown as SEQ ID NO. 55 and a heavy chain having amino acid sequence shown as SEQ ID NO. 53, the DFPD1-3 comprising a light chain having amino acid sequence shown as SEQ ID NO. 56 and a heavy chain having amino acid sequence shown as SEQ ID NO. 53, the DFPD1-4 comprising a light chain having amino acid sequence shown as SEQ ID NO. 57 and a heavy chain having amino acid sequence shown as SEQ ID NO. 53, the DFPD1-5 comprising a light chain having amino acid sequence shown as SEQ ID NO. 58 and a heavy chain having amino acid sequence shown as SEQ ID NO. 53, the DFPD1-6 comprising a light chain having amino acid sequence shown as SEQ ID NO. 59 and a heavy chain having amino acid sequence shown as SEQ ID NO. 53, the DFPD1-7 comprising a light chain having amino acid sequence shown as SEQ ID NO. 60 and a heavy chain having amino acid sequence shown as SEQ ID NO. 53.

3. Determining the Affinity of the Anti-PD-1 Antibody's ScFv by Gradient Diluting Phage-ELISA Displaying and purifying the phage of clones obtained by example 2, the affinity of the phage-Abs was determined by a gradient diluting phage-ELISA test.

Figure 7:
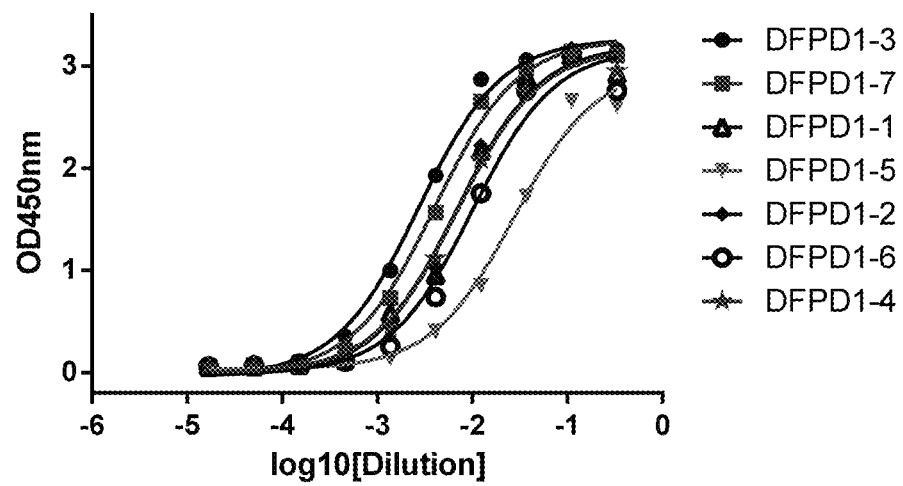
FIG. 7 shows relative affinity identification of the phage-Abs selected from the mutant light chain variable region library by gradient diluting phage-ELISA.

The PD1-His in pH9.6 carbonate buffer solution was used for coating at 4° C. overnight. PBST was used for washing for three times, 4% skim milk-PBST was used for blocking at 37° C. for one hour. The purified phases were diluted for three times with 4% milk-PBST, then 100 µL diluted sample was added into each well. After setting at room temperature for one hour, the ELISA plate was washed with PBST, then the anti-M13-HRP monoclonal antibody diluted in 4% skim milk was added into the ELISA plate. After placing for one hour at room temperature, the wells were stained with TMB stain solution kit for five minutes at room temperature. The reaction was stopped with 50 µL of 2 mol/L H2504 per well, and the optical density was determined with the microplate reader by reading at 450 nm wavelength. The result shows a number of different phage antibodies selected can be combined with PD-1, further the affinity of DFPD1-3 and DFPD1-7 are significantly higher than other clones (as shown in FIG. 7). DFPD1-3 and DFPD1-7 were selected for further experiments.

Example 4

The Affinity Maturation Test In Vitro of the Anti-PD-1 of Single-Chain Antibody DFPD1-3 and DFPD1-7

1. The Construction of the Heavy Chain CDR1, CDR 2 and CDR 3 Mutant Library for DFPD1-3 and DFPD1-7.

Figure 8:
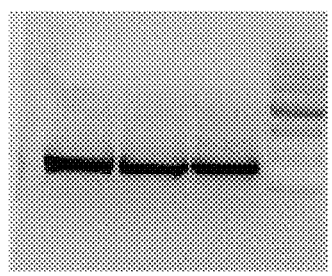
FIG. 8 shows that the electrophoresis atlas of the PCR product by using the synthetic mutant heavy chain variable domain library as a template in building the mutant heavy chain variable region library.
Figure 9:
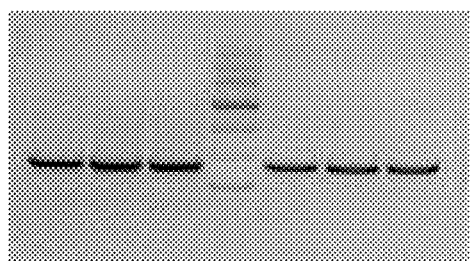
FIG. 9 shows that the electrophoresis atlas of the PCR product of the light chain and the linker by using the plasmid DFPD1-3 and DFPD1-7 as template in building the mutant heavy chain variable region library.

Using the synthesized heavy chain mutant library (as shown in SEQ ID NO. 13) as a template and PVHF2 and PVHR2 as PCR primers, the heavy chain gene library (as shown in FIG. 8) were amplified by PCR; the PVLF2 and PVLR2 as PCR primers and plasmid DFPD1-3 and DFPD1-7 were used as the template to amplify its light chain and its linker (as shown in FIG. 9). Wherein, the left is DFPD1-3, the right is DFPD1-7. Reaction conditions: 95° C. for 30 seconds, 1 cycle, 95° C. for 15 seconds, 60° C. for 10 seconds, 72° C. for 30 seconds, 3 cycles, 95° C. for 15 seconds, 72° C. for 40 seconds, 25 cycles, 72° C. for 5 minutes, 4° C. for storing. PCR products were recovered with universal recovery kit.

The sequences of primers as following:

(SEQ ID NO. 49)
PVHF2: 5'-CATACCATGGCCCAGGTGCAGCTGGTGGAGTCTG-3'

(SEQ ID NO. 50)
PVHR2: 5'-TGAGGAGACGGTGACCAGGGTGCCCTG -3'

(SEQ ID NO. 51)
PVLF2: 5'-CTGGTCACCGTCTCCTCAGGTGGTGGTGGTAGC-3'

(SEQ ID NO. 52)
PVLR2: 5'-CTAAGCGGCCGCTTTGATCTCCACTTTGGTGC-3'

Figure 10:
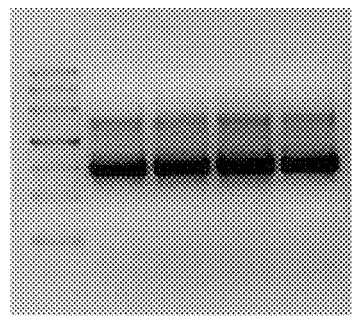
FIG. 10 shows the electrophoresis atlas of the PCR product of the mutant library obtained by amplification in building the mutant heavy chain variable region library VHCDR123M-DFPD1-3.
Figure 11:
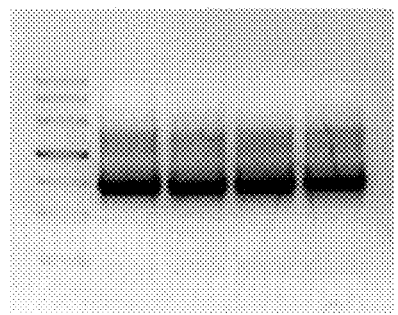
FIG. 11 shows the electrophoresis atlas of the PCR product of the mutant library obtained by amplification in building the mutant heavy chain variable region library VHCDR123M-DFPD1-7.

The above two PCR products were amplified by overlap PCR to obtain the gene of DFPD1-3 and DFPD1-7 heavy chain mutation library. Reaction conditions: 95° C. for 30 seconds, 1 cycle, 95° C. for 15 seconds, 72° C. for 30 seconds, 4 cycles (added the primers PVHF2 and PVLR2), 95° C. for 15 seconds, 72° C. for 40 seconds, 25 cycles, 72° C. for 5 minutes, 4° C. for storing. PCR products were recovered with universal recovery kit, the corresponding products named as VHCDR123M-DFPD1-3 (as shown in FIG. 10) and VHCDR123M-DFPD1-7 (as shown in FIG. 11).

VHCDR123M-DFPD1-3, VHCDR123M-DFPD1-7 and plasmid pScFvDisb-s were digested with NcoI-HF and NotI, and the enzyme-digested products were separated by 0.8% agarose gel electrophoresis (as shown in FIG. 5). After gel extraction, the enzyme-digested products were purified with a commercial available DNA purification kit. The digested PCR products and pScFvDisb-s were ligated at the molar ratio of 4:1 with T4 DNA ligase for 16° C. for 4 hours. The ligated products were transformed into TG1 competent cells by the electroporation. After recovering cells in SOC medium at 37° C. for one hour, a small fraction of the bacteria was used to plate on a culture dish to estimate the capacity of the antibody library. The remaining bacteria were centrifuged at room temperature at 4000 rpm for 15 minutes, and then the supernatant was removed. The precipitation was plated on 2 YTAG large culture dish that was culturing at 37° C. overnight.

Two different antibody libraries were made; the capacity of each antibody library is about $10^7$, the capacity of the antibody library is much higher than the diversity. Twenty clones from the above antibody library randomly were sequenced, the sequences showed 90% accuracy.

Figure 12:
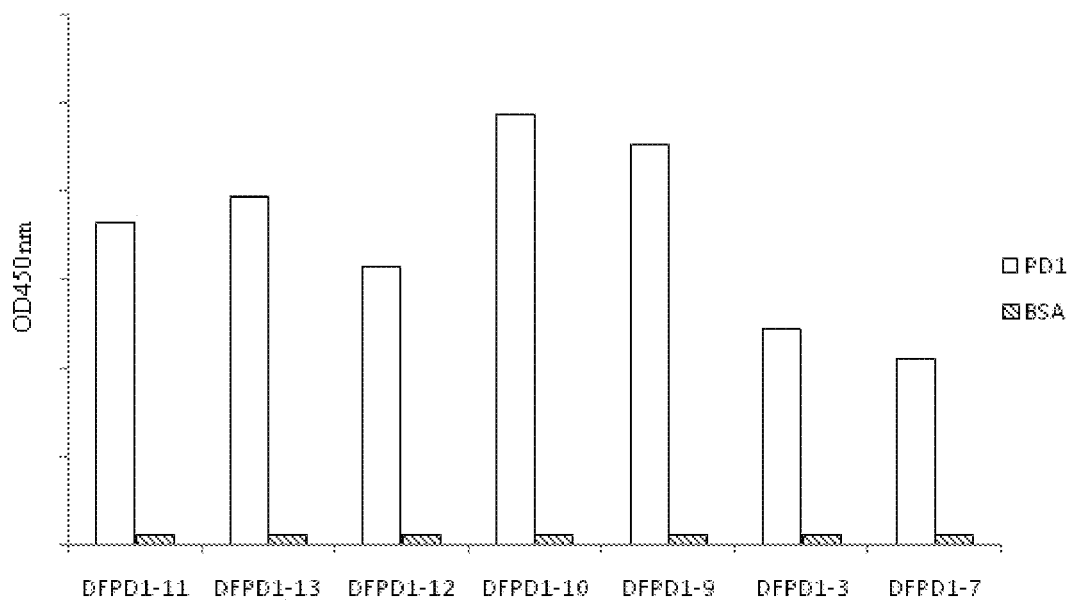
FIG. 12 shows relative affinity identification of the phage-Abs selected from the mutant heavy chain variable region library by monoclonal phage-ELISA.

2. Bio-Panning of the Phage Antibody Library and the Screening of Positive Clones The above two antibody libraries were displayed, precipitated and purified on the phage level. Then the anti-PD-1 ScFv form antibodies were bio-panned from these libraries. The method of bio-panning the phage antibody libraries is the same as example 1. The method of screening the positive clones of the anti-PD-1 antibody's ScFv is the same as example 2. The result shows five different anti-PD-1 antibodies were screened. They are named as DFPD1-9, DFPD1-10, DFPD1-11, DFPD1-12, DFPD1-13. Wherein the light chain variable region sequence of DFPD1-9, DFPD1-11 and DFPD1-12 is DFPD1-L3; and the light chain variable region sequence of DFPD1-10 and DFPD1-13 is DFPD1-L7; and the heavy chain variable region sequence of DFPD1-9 and DFPD1-10 is DFPD1-H2; the heavy chain variable region sequence of DFPD1-11 and DFPD1-13 is DFPD1-H3; the heavy chain variable region sequence of DFPD1-12 is DFPD1-H4. The relative affinity of the monoclonal phage was determined by ELISA as shown in FIG. 12.

Figure 13:
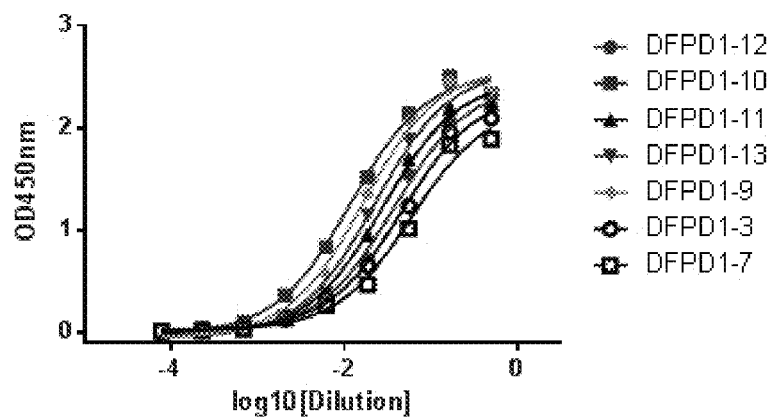
FIG. 13 shows the relative affinity identification of phage-Abs selected from the mutant heavy chain variable region library by gradient diluting phage-ELISA.

3. Determining the Affinity of the Anti-PD-1 Antibody's ScFv by a Gradient Diluting Phage-ELISA Displaying and purifying the clones were done as descripted in the second implementation of this example at the level of monoclonal phage; the affinity of the phage-Abs was determined by a gradient diluting phage-ELISA test, and the method is the same as the third implementation of the example 3. The result shows a number of different phage antibodies can interact with PD-1. There is no obvious affinity difference among this phage antibodies (as shown in FIG. 13), wherein DFPD1-9, DFPD1-10, DFPD1-11, DFPD1-12 and DFPD1-13 are better, and are used for the further experiments.

Example 5

The Determination of the Affinity of the Anti-PD-1 Monoclonal Antibodies, DFPD1-9, DFPD1-10, DFPD1-11, DFPD1-12 and DFPD1-13

1. The Preparing of Anti-PD-1 Full-Length Antibody

Figure 14:
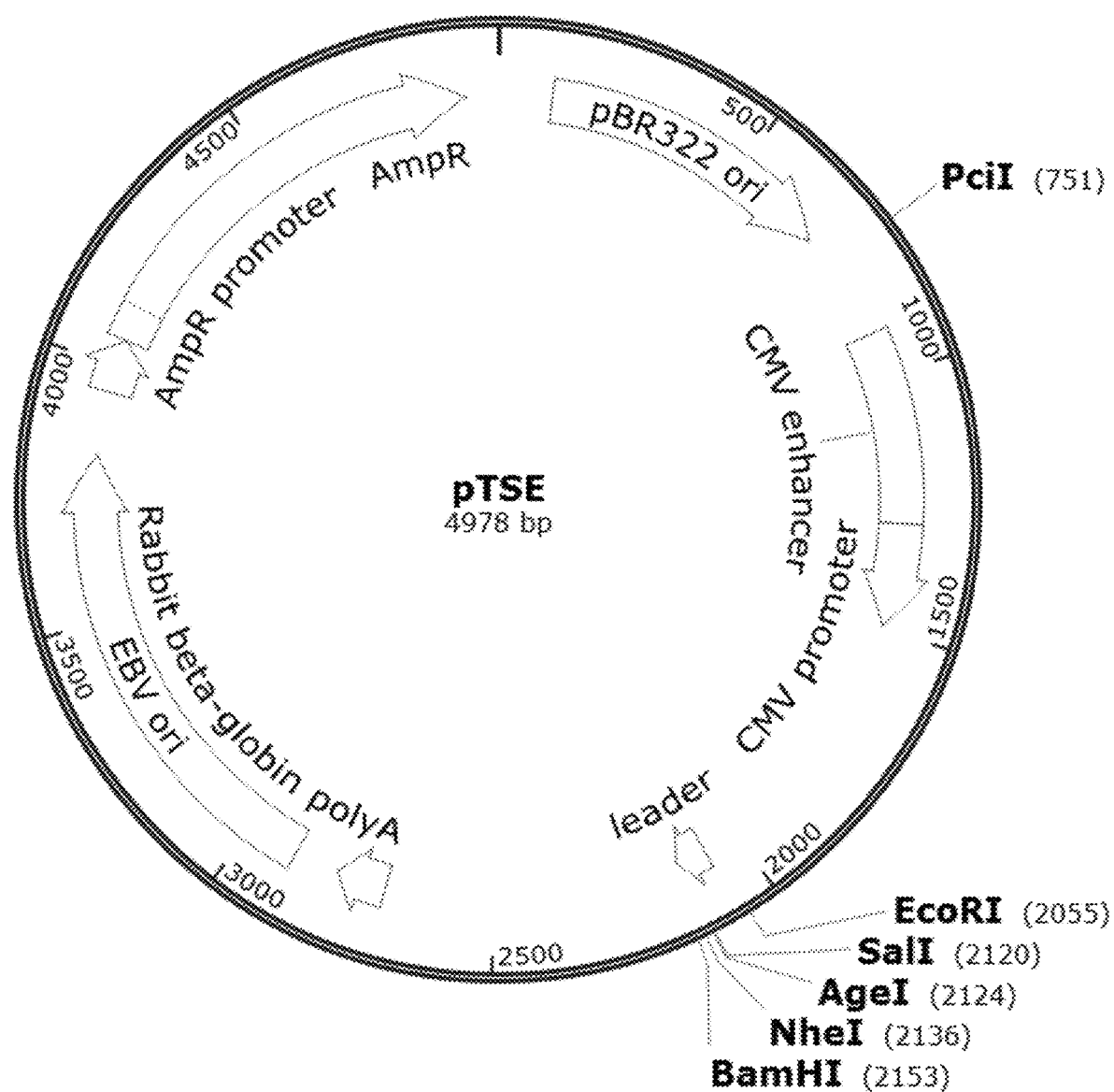
FIG. 14 shows the plasmid vector map of pTSE.

The DNAs encoding above antibodies' heavy chain VH and light chain VK were cloned into vector pTSE, respectively, with the DNAs encoding the heavy chain constant region, the light chain constant region (as shown in FIG. 14), the constant region γ4 (as shown in SEQ ID NO. 16) and κ (as shown in SEQ ID NO. 15) of human (the vector atlas of pTSE as shown in FIG. 14, the preparation process as shown in the description page 3 section 0019 of CN103525868A), wherein the DFPD1-9 comprising a light chain having amino acid sequence shown as SEQ ID NO. 56 and a heavy chain having amino acid sequence shown as SEQ ID NO. 61, the DFPD1-10 comprising a light chain having amino acid sequence shown as SEQ ID NO. 60 and a heavy chain having amino acid sequence shown as SEQ ID NO. 61, the DFPD1-11 comprising a light chain having amino acid sequence shown as SEQ ID NO. 56 and a heavy chain having amino acid sequence shown as SEQ ID NO. 62, the DFPD1-12 comprising a light chain having amino acid sequence shown as SEQ ID NO. 56 and a heavy chain having amino acid sequence shown as SEQ ID NO. 63 and the DFPD1-13 comprising a light chain having amino acid sequence shown as SEQ ID NO. 60 and a heavy chain having amino acid sequence shown as SEQ ID NO. 62. Transient transfected HEK293E cells with the cloned vector were used to express antibodies. The antibody proteins were purified with protein A affinity column by the AKTA.

2. The Determination of the Affinity of the Monoclonal Antibody with BIAcore X100

The affinity of the antibodies were determined by ligand-capture method. Anti-human IgG was coupled to the surface of CM5 chip, and DFPD1-9, DFPD1-10, DFPD1-11, DFPD1-12 and DFPD1-13 were diluted respectively to ensure the capturing about 300 RU of the antibody by the anti-human IgG. A series of concentration gradient of the PD-1 (1000 nM, 500 nM, 250 nM, 125 nM, 62.5 nM, 31.25 nM, 15.625 nM, 7.8125 nM, 3.9063 nM, 1.9531 nM and 0.9766 nM), flowed through the surface of the stationary phase to determine the affinities of the antibodies. The results show the affinity of the antibodies has no obvious difference (as shown in table 2).

TABLE 2

Determination Of The Affinity Constants For The Anti-PD 1 Full-length Antibody

| Sample | ka (1/Ms) | kd (1/s) | KD |
|---|---|---|---|
| DFPD1-9  | 1.626E+4 | 1.045E-4 | 6.429E-9 |
| DFPD1-10 | 3.285E+4 | 1.300E-4 | 3.957E-9 |
| DFPD1-11 | 9.357E+3 | 1.015E-4 | 1.085E-8 |
| DFPD1-12 | 1.327E+4 | 2.975E-4 | 2.242E-8 |
| DFPD1-13 | 1.811E+4 | 1.079E-4 | 9.504E-9 |

3. The Binding Assay of the Anti-PD-1 Antibody

Figure 15:
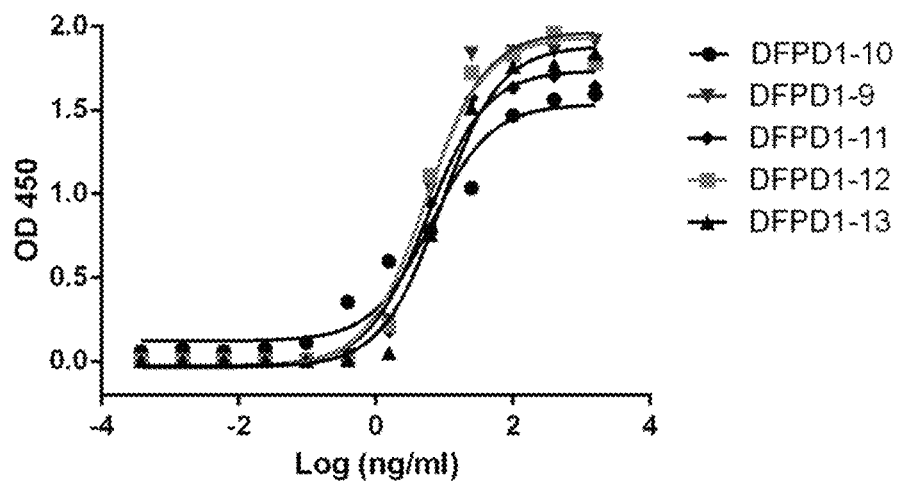
FIG. 15 shows the binding activities of monoclonal antibodies to PD-1 at the protein level.

PD-1-His in pH9.6 carbonate buffer solution, 60 ng/well/ 100 µL, was used for coating 96 well plate at 4° C. overnight. After washing five times with 300 µl/well PBST, the wells were blocked for two hours with 1% BSA-PBS at 37° C. Different dilution of the antibodies DFPD1-9, DFPD1-10, DFPD1-11, DFPD1-12 and DFPD1-13 were added. The highest concentration of these five kinds of antibodies is 16 µg/mL, diluted for 4 times to 11 gradients, and the last well was used as the negative control which was added PBS diluent only. After incubating at 37° C. for one hour, the wells were washed five times with 300 µL/well of PBST, then adding the anti-human Fc-HRP secondary antibodies diluted at 1:40000 with 1% BSA-PBS, incubating at 37° C. for one hour. After staining with TMB stain solution kit, 100 µL/well, for 8 minutes at room temperature, the reaction was stopped with 504 of 2 mol/L $H_2SO_4$/well, and the optical density was determined at 450 nm and 630 nm wavelength. The result is shown in FIG. 15, all antibodies can bind with PD-1.

4. The Antibody Competitive Inhibition Test of PD-L1 Binding with PD-1

Figure 16:
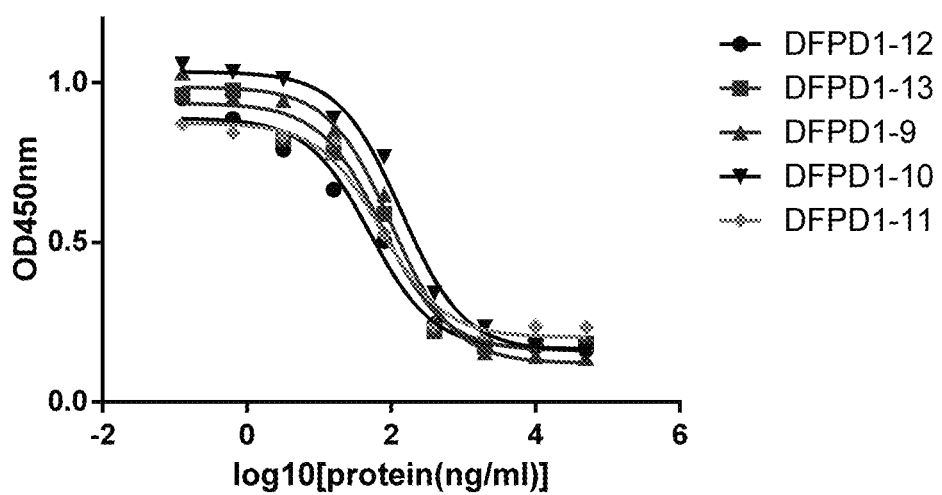
FIG. 16 shows the competitive inhibition of PD-1 binding to PD-L1 by full antibodies.

PDL1-Fc in pH9.6 carbonate buffer solution was used for coating plates at 4° C. for overnight. After washing five times with PBST, the wells were blocked for two hours with 1% BSA-PBS at 37° C. The following five antibodies with 4 µg/mL PD1-His, DFPD1-9, DFPD1-10, DFPD1-11, DFPD1-12 and DFPD1-13 were diluted respectively, starting from the molar ratio 10:1 of the antibody and PD-1-His, the gradient diluting for five times and 9 dilution gradient of each sample. After incubating at 37° C. for one hour, the wells were washed five times with PBST, and then the mouse anti-His antibody HRP labeled with 1% BSA-PBS diluted were added. After incubating at 37° C. for one hour, the wells were stained with TMB stain solution kit, 100 µL/well, for 8 minutes at room temperature. The reaction was stopped with 504 of 10% $H_2SO_4$/well. The optical density was read at 450 nm and 630 nm wavelength. The result is shown in FIG. 16, DFPD1-9, DFPD1-10, DFPD1-11, DFPD1-12 and DFPD1-13 can inhibit the binding of PD-1 and PD-L1.

Example 6

The Binding Assay of Anti-PD-1 Antibody and Cell-Surface PD-1

Firstly, the CHO cell line with stable PD-1 over-expression was made and named PD1-CHO. After coating 96-well plates with gelatin, PD1-CHO cells was digested by trypsin and then stopped. After centrifuging and suspending these cells, the cells were diluted to $2\times10^5$ cells/mL, 100 µL per well in 96-well plates, totally 12 well×6 row, namely $2\times10^4$ cells/well, and cultured at 5% $CO_2$, 37° C. overnight. The culture medium were discarded the next day, and the wells were washed one time with 350 µL precooling PBS. Freshly prepared 2% PFA was added to fix 5 minutes, and then PBS was used to wash two times.

Figure 17:
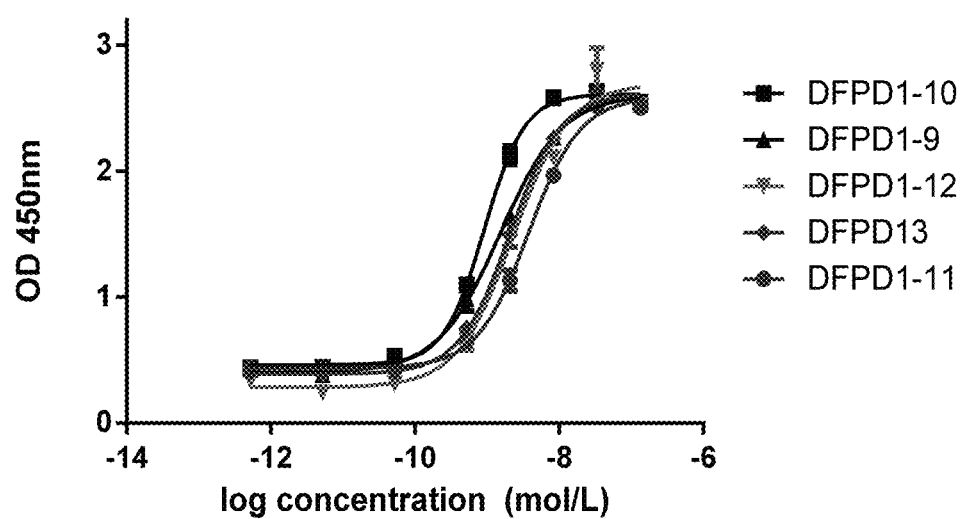
FIG. 17 shows the binding activities of monoclonal antibodies to PD-1 on the cell surface.

The full-length anti-PD-1 antibody of double dilution was added into the cell plates, the diluent is PBS with 0.5% BSA. Sample concentration started from 100 µg/mL, diluting for 8 times, totally 12 gradients of dilution. After incubating for 30 minutes at room temperature, supernatant was discarded, and wells were washed three times with 350 µL PBS. The anti-human Fc-HRP Secondary antibodies diluted at 1:5000 were added, and incubated for 15 minutes at room temperature. After washing three times with 350 µL PBS, 100 µL TMB stain solution was added into each well, staining for 15 to 30 minutes at room temperature. After adding 50 µL2 mol/L H2504 per well to stop the staining, the optical density was read at 450 nm wavelength with the microplate reader. The results were processed with Graph pad prism software, and the binding constant was calculated (as shown in FIG. 17).

The invention includes all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

What is claimed is:

1. An anti-PD-1 monoclonal antibody comprises light chain and heavy chain, wherein the anti-PD-1 monoclonal antibody is DFPD1-10 that comprising a light chain having the amino acid sequence shown as SEQ ID NO: 60 and a heavy chain having the amino acid sequence shown as SEQ ID NO: 61.

2. The anti-PD-1 monoclonal antibody according to claim 1, wherein the anti-PD-1 monoclonal antibody is a bi-specific antibody or a drug-conjugated antibody.

3. The anti-PD-1 monoclonal antibody according to claim 1, wherein the anti-PD-1 monoclonal antibody is for treating a human cancer.

4. The anti-PD-1 monoclonal antibody according to claim 1, wherein the anti-PD-1 monoclonal antibody is for detecting the expression of PD-1 protein.

* * * * *

SEQUENCE LISTING

<160> NUMBER OF SEQ ID NOS: 74

<210> SEQ ID NO 1
<211> LENGTH: 113
<212> TYPE: PRT
<213> ORGANISM: Artificial Sequence
<220> FEATURE:
<223> OTHER INFORMATION: The sequence is synthesized

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Asn
            20                  25                  30

Gly Met His Trp Val Arg Gln Ala Pro Gly Lys Gly Leu Glu Trp Val
        35                  40                  45

Ala Val Ile Trp Tyr Asp Ser Thr Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Thr Asp Tyr Trp Gly Gln Gly Thr Leu Val Thr Val Ser
            100                 105                 110

Ser

<210> SEQ ID NO 2
<211> LENGTH: 113
<212> TYPE: PRT
<213> ORGANISM: Artificial Sequence
<220> FEATURE:
<223> OTHER INFORMATION: The sequence is synthesized

<400> SEQUENCE: 2

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Ser Ser Arg Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser

<210> SEQ ID NO 3
<211> LENGTH: 113
<212> TYPE: PRT
<213> ORGANISM: Artificial Sequence
<220> FEATURE:
<223> OTHER INFORMATION: The sequence is synthesized

<400> SEQUENCE: 3

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Asn
            20                  25                  30

Gly Met His Trp Val Arg Gln Ala Pro Gly Lys Gly Leu Glu Trp Val
        35                  40                  45

Ala Val Ile Trp Tyr Asp Ser Ser Arg Lys Tyr Tyr Ala Asp Ser Val
    50                  55                  60

Lys Gly Arg Phe Thr Ile Ser Arg Asp Asn Ser Lys Asn Thr Leu Phe

```
                65                  70                  75                  80
Leu Gln Met Asn Ser Leu Arg Ala Glu Asp Thr Ala Val Tyr Tyr Cys
                    85                  90                  95

Ala Thr Asn Asn Asp Tyr Trp Gly Gln Gly Thr Leu Val Thr Val Ser
                100                 105                 110

Ser

<210> SEQ ID NO 4
<211> LENGTH: 113
<212> TYPE: PRT
<213> ORGANISM: Artificial Sequence
<220> FEATURE:
<223> OTHER INFORMATION: The sequence is synthesized

<400> SEQUENCE: 4

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                    85                  90                  95

Ala Thr Asn Asn Asp Tyr Trp Gly Gln Gly Thr Leu Val Thr Val Ser
                100                 105                 110

Ser

<210> SEQ ID NO 5
<211> LENGTH: 107
<212> TYPE: PRT
<213> ORGANISM: Artificial Sequence
<220> FEATURE:
<223> OTHER INFORMATION: The sequence is synthesized

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile His Ser Tyr
                20                  25                  30

Leu Asp Trp Tyr Gln Gln Lys Pro Gly Lys Ala Pro Lys Leu Leu Ile
            35                  40                  45

Tyr Glu Ala Ser Thr Arg Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Lys Leu Pro Ile
                    85                  90                  95

Thr Phe Gly Gln Gly Thr Lys Val Glu Ile Lys
                100                 105

<210> SEQ ID NO 6
<211> LENGTH: 107
<212> TYPE: PRT
<213> ORGANISM: Artificial Sequence
```

<220> FEATURE:
<223> OTHER INFORMATION: The sequence is synthesized

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Ser Asn Trp
            20                  25                  30

Leu Asp Trp Tyr Gln Gln Lys Pro Gly Lys Ala Pro Lys Leu Leu Ile
        35                  40                  45

Tyr Asp Ala Ser Asn Arg Ala Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg His Ile Pro Leu
                85                  90                  95

Thr Phe Gly Gln Gly Thr Lys Val Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: The sequence is synthesized

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile His Asn Tyr
            20                  25                  30

Leu Asp Trp Tyr Gln Gln Lys Pro Gly Lys Ala Pro Lys Leu Leu Ile
        35                  40                  45

Tyr Asn Ala Ser Thr Arg Ala Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Leu His Leu Pro Leu
                85                  90                  95

Thr Phe Gly Gln Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: The sequence is synthesized

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Trp
            20                  25                  30

Leu Asp Trp Tyr Gln Gln Lys Pro Gly Lys Ala Pro Lys Leu Leu Ile
        35                  40                  45

Tyr Asp Ala Ser Thr Leu Ala Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Val Asn Leu Pro Leu
            85                  90                  95

Thr Phe Gly Gln Gly Thr Lys Val Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: The sequence is synthesized

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Arg Asn Tyr
            20                  25                  30

Leu Asp Trp Tyr Gln Gln Lys Pro Gly Lys Ala Pro Lys Leu Leu Ile
        35                  40                  45

Tyr Gly Ala Ser Thr Arg Ala Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Asp Leu Pro Leu
            85                  90                  95

Thr Phe Gly Gln Gly Thr Lys Val Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: The sequence is synthesized

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Trp
            20                  25                  30

Leu Asp Trp Tyr Gln Gln Lys Pro Gly Lys Ala Pro Lys Leu Leu Ile
        35                  40                  45

Tyr Asp Ala Ser Thr Arg Ala Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Leu Pro Leu
            85                  90                  95

Thr Phe Gly Gln Gly Thr Lys Val Glu Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: The sequence is synthesized

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Asn Tyr
            20                  25                  30

Leu Asp Trp Tyr Gln Gln Lys Pro Gly Lys Ala Pro Lys Leu Leu Ile
        35                  40                  45

Tyr Asp Ala Ser Thr Arg Ala Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Met Gln Leu Pro Leu
                85                  90                  95

Thr Phe Gly Gln Gly Thr Lys Val Glu Ile Lys
            100                 105

<210> SEQ ID NO 12
<211> LENGTH: 321
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (271)..(272)
<223> OTHER INFORMATION: n is a, c, g, or t
<220> FEATURE:
<221> NAME/KEY: misc_feature
<222> LOCATION: (274)..(275)
<223> OTHER INFORMATION: n is a, c, g, or t
<220> FEATURE:
<221> NAME/KEY: misc_feature
<222> LOCATION: (280)..(281)
<223> OTHER INFORMATION: n is a, c, g, or t
<220> FEATURE:
<221> NAME/KEY: misc_feature
<222> LOCATION: (286)..(287)
<223> OTHER INFORMATION: n is a, c, g, or t

<400> SEQUENCE: 12
gatatccaga tgacccagag cccgagcagc ctgagcgcga gcgtgggtga tcgcgtgacc     60
attacctgcc gcgcgagcca grrtrtcvrt avcnbyctgr mttggtatca gcagaaaccg    120
ggtaaagcgc cgaaactgtt aatttatrvk gccagcavcc kgsmgwctgg cgtgccgtcg    180
cgttttagcg gctcgggttc gggcaccgat tttaccctga ccatctcgag cttgcagccg    240
gaggacttcg ccacctacta ttgccagcaa nnsnnsvrbn nsccannsac cttcggtcag    300
ggcaccaaag tggagatcaa a                                              321

<210> SEQ ID NO 13
<211> LENGTH: 339
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (280)..(281)

```
<223> OTHER INFORMATION: n is a, c, g, or t
<220> FEATURE:
<221> NAME/KEY: misc_feature
<222> LOCATION: (283)..(284)
<223> OTHER INFORMATION: n is a, c, g, or t
<220> FEATURE:
<221> NAME/KEY: misc_feature
<222> LOCATION: (286)..(287)
<223> OTHER INFORMATION: n is a, c, g, or t
<220> FEATURE:
<221> NAME/KEY: misc_feature
<222> LOCATION: (289)..(290)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t
<220> FEATURE:
<221> NAME/KEY: misc_feature
<222> LOCATION: (295)..(296)
<223> OTHER INFORMATION: n is a, c, g, or t

<400> SEQUENCE: 13
```

| | | | | | |
|---|---|---|---|---|---|
| caggtgcagc | tggtggagtc | tgggggaggc | gtggtccagc | ctgggaggtc | cctgagactc | 60 |
| gattgtaagg | cgtctggaat | caccttcagt | rvytacksga | tgmrytgggt | ccgccaggct | 120 |
| ccaggcaagg | ggctggagtg | ggtgkcmkky | attarnkvyr | ryggcrrywm | yamrtactat | 180 |
| gcagactccg | tgaagggccg | attcaccatc | tccagagaca | attccaagaa | cacgctgttt | 240 |
| ctgcaaatga | acagcctgag | agccgaggac | acggrrvvsn | nynnsnnsnn | ynnsnnshtk | 300 |
| gattactggg | gccagggcac | cctggtcacc | gtctcctca | | | 339 |

```
<210> SEQ ID NO 14
<211> LENGTH: 993
<212> TYPE: DNA
<213> ORGANISM: Artificial Sequence
<220> FEATURE:
<223> OTHER INFORMATION: The sequence is synthesized

<400> SEQUENCE: 14
```

| | | | | | |
|---|---|---|---|---|---|
| gtgtcctccg | cctccaccaa | gggcccttcc | gtgttccctc | tggccccttg | ctcccgctcc | 60 |
| acctccgagt | ccaccgccgc | cctgggctgc | ctggtgaagg | actacttccc | tgagcctgtg | 120 |
| accgtgtcct | ggaactccgg | cgccctgacc | tccggcgtgc | acaccttccc | tgccgtgctg | 180 |
| cagtcctccg | gcctgtactc | cctgtcctcc | gtggtgaccg | tgccttcctc | ctccctgggc | 240 |
| accaagacct | acacctgcaa | cgtggaccac | aagccttcca | caccaaggt | ggacaagcgc | 300 |
| gtggagtcca | agtacggccc | ctcttgccct | ccttgccctg | ccctgagtt | cctgggcggc | 360 |
| ccttccgtgt | tcctgttccc | tcctaagcct | aaggacaccc | tgatgatctc | ccgcacccct | 420 |
| gaggtgacct | gcgtggtggt | ggacgtgtcc | caggaggacc | ctgaggtgca | gttcaactgg | 480 |
| tacgtggacg | gcgtggaggt | gcacaacgcc | aagaccaagc | ctcgcgagga | gcagttcaac | 540 |
| tccacctacc | gcgtggtgtc | cgtgctgacc | gtgctgcacc | aggactggct | gaacggcaag | 600 |
| gagtacaagt | gcaaggtgtc | caacaagggc | ctgccttcct | ccatcgagaa | gaccatctcc | 660 |
| aaggccaagg | gccagcctcg | cgagcctcag | gtgtacaccc | tgcctccttc | ccaggaggag | 720 |
| atgaccaaga | accaggtgtc | cctgacctgc | ctggtgaagg | gcttctaccc | ttccgacatc | 780 |
| gccgtggagt | gggagtccaa | cggccagcct | gagaacaact | acaagaccac | ccctcctgtg | 840 |
| ctggactccg | acggctcctt | cttcctgtac | tcccgcctga | ccgtggacaa | gtcccgctgg | 900 |
| caggagggca | acgtgttctc | ctgctccgtg | atgcacgagg | ccctgcacaa | ccactacacc | 960 |
| cagaagtccc | tgtccctgtc | cctgggcaag | tag | | | 993 |

<210> SEQ ID NO 15
<211> LENGTH: 107
<212> TYPE: PRT
<213> ORGANISM: Artificial Sequence
<220> FEATURE:
<223> OTHER INFORMATION: The sequence is synthesized

<400> SEQUENCE: 15

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 16
<211> LENGTH: 330
<212> TYPE: PRT
<213> ORGANISM: Artificial Sequence
<220> FEATURE:
<223> OTHER INFORMATION: The sequence is synthesized

<400> SEQUENCE: 16

```
Val Ser Ser Ala Ser Thr Lys Gly Pro Ser Val Phe Pro Leu Ala Pro
1               5                   10                  15

Cys Ser Arg Ser Thr Ser Glu Ser Thr Ala Ala Leu Gly Cys Leu Val
            20                  25                  30

Lys Asp Tyr Phe Pro Glu Pro Val Thr Val Ser Trp Asn Ser Gly Ala
        35                  40                  45

Leu Thr Ser Gly Val His Thr Phe Pro Ala Val Leu Gln Ser Ser Gly
    50                  55                  60

Leu Tyr Ser Leu Ser Ser Val Val Thr Val Pro Ser Ser Ser Leu Gly
65                  70                  75                  80

Thr Lys Thr Tyr Thr Cys Asn Val Asp His Lys Pro Ser Asn Thr Lys
                85                  90                  95

Val Asp Lys Arg Val Glu Ser Lys Tyr Gly Pro Pro Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
                195                 200                 205
Lys Gly Leu Pro Ser Ser Ile Glu Lys Thr Ile Ser Lys Ala Lys Gly
    210                 215                 220
Gln Pro Arg Glu Pro Gln Val Tyr Thr Leu Pro Pro Ser Gln Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Arg Leu Thr Val Asp Lys Ser Arg Trp Gln Glu Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Leu Gly Lys
                325                 330

<210> SEQ ID NO 17
<211> LENGTH: 321
<212> TYPE: DNA
<213> ORGANISM: Artificial Sequence
<220> FEATURE:
<223> OTHER INFORMATION: The sequence is synthesized

<400> SEQUENCE: 17
cgtacggtgg cggcgccatc tgtcttcatc ttcccgccat ctgatgagca gttgaaatct      60
ggtaccgcta gcgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 18
<211> LENGTH: 11
<212> TYPE: PRT
<213> ORGANISM: Artificial Sequence
<220> FEATURE:
<223> OTHER INFORMATION: The sequence is synthesized

<400> SEQUENCE: 18

Arg Ala Ser Gln Asn Ile His Ser Tyr Leu Asp
1               5                   10

<210> SEQ ID NO 19
<211> LENGTH: 11
<212> TYPE: PRT
<213> ORGANISM: Artificial Sequence
<220> FEATURE:
<223> OTHER INFORMATION: The sequence is synthesized

<400> SEQUENCE: 19

Arg Ala Ser Gln Asn Val Ser Asn Trp Leu Asp
1               5                   10

<210> SEQ ID NO 20
<211> LENGTH: 11
<212> TYPE: PRT
<213> ORGANISM: Artificial Sequence
```

```
<220> FEATURE:
<223> OTHER INFORMATION: The sequence is synthesized

<400> SEQUENCE: 20

Arg Ala Ser Gln Ser Ile His Asn Tyr Leu Asp
1               5                   10

<210> SEQ ID NO 21
<211> LENGTH: 11
<212> TYPE: PRT
<213> ORGANISM: Artificial Sequence
<220> FEATURE:
<223> OTHER INFORMATION: The sequence is synthesized

<400> SEQUENCE: 21

Arg Ala Ser Gln Asp Ile Asn Asn Trp Leu Asp
1               5                   10

<210> SEQ ID NO 22
<211> LENGTH: 11
<212> TYPE: PRT
<213> ORGANISM: Artificial Sequence
<220> FEATURE:
<223> OTHER INFORMATION: The sequence is synthesized

<400> SEQUENCE: 22

Arg Ala Ser Gln Asp Val Arg Asn Tyr Leu Asp
1               5                   10

<210> SEQ ID NO 23
<211> LENGTH: 11
<212> TYPE: PRT
<213> ORGANISM: Artificial Sequence
<220> FEATURE:
<223> OTHER INFORMATION: The sequence is synthesized

<400> SEQUENCE: 23

Arg Ala Ser Gln Gly Ile Asn Ser Trp Leu Asp
1               5                   10

<210> SEQ ID NO 24
<211> LENGTH: 11
<212> TYPE: PRT
<213> ORGANISM: Artificial Sequence
<220> FEATURE:
<223> OTHER INFORMATION: The sequence is synthesized

<400> SEQUENCE: 24

Arg Ala Ser Gln Ser Val Ser Asn Tyr Leu Asp
1               5                   10

<210> SEQ ID NO 25
<211> LENGTH: 7
<212> TYPE: PRT
<213> ORGANISM: Artificial Sequence
<220> FEATURE:
<223> OTHER INFORMATION: The sequence is synthesized

<400> SEQUENCE: 25

Glu Ala Ser Thr Arg Ala Ser
1               5

<210> SEQ ID NO 26
<211> LENGTH: 7
<212> TYPE: PRT
<213> ORGANISM: Artificial Sequence
<220> FEATURE:
```

```
<223> OTHER INFORMATION: The sequence is synthesized

<400> SEQUENCE: 26

Asp Ala Ser Asn Arg Ala Thr
1               5

<210> SEQ ID NO 27
<211> LENGTH: 7
<212> TYPE: PRT
<213> ORGANISM: Artificial Sequence
<220> FEATURE:
<223> OTHER INFORMATION: The sequence is synthesized

<400> SEQUENCE: 27

Asn Ala Ser Thr Arg Ala Thr
1               5

<210> SEQ ID NO 28
<211> LENGTH: 7
<212> TYPE: PRT
<213> ORGANISM: Artificial Sequence
<220> FEATURE:
<223> OTHER INFORMATION: The sequence is synthesized

<400> SEQUENCE: 28

Asp Ala Ser Thr Leu Ala Thr
1               5

<210> SEQ ID NO 29
<211> LENGTH: 7
<212> TYPE: PRT
<213> ORGANISM: Artificial Sequence
<220> FEATURE:
<223> OTHER INFORMATION: The sequence is synthesized

<400> SEQUENCE: 29

Gly Ala Ser Thr Arg Ala Thr
1               5

<210> SEQ ID NO 30
<211> LENGTH: 7
<212> TYPE: PRT
<213> ORGANISM: Artificial Sequence
<220> FEATURE:
<223> OTHER INFORMATION: The sequence is synthesized

<400> SEQUENCE: 30

Asp Ala Ser Thr Arg Ala Thr
1               5

<210> SEQ ID NO 31
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 31

Gln Gln Ala Leu Lys Leu Pro Ile Thr
1               5

<210> SEQ ID NO 32
<211> LENGTH: 9
<212> TYPE: PRT
<213> ORGANISM: Artificial Sequence
<220> FEATURE:
<223> OTHER INFORMATION: The sequence is synthesized
```

<400> SEQUENCE: 32

Gln Gln Ser Arg His Ile Pro Leu Thr
1               5

<210> SEQ ID NO 33
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 33

Gln Gln Glu Leu His Leu Pro Leu Thr
1               5

<210> SEQ ID NO 34
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 34

Gln Gln Asn Val Asn Leu Pro Leu Thr
1               5

<210> SEQ ID NO 35
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 35

Gln Gln Asp Ile Asp Leu Pro Leu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 36

Gln Gln Ser Tyr Arg Leu Pro Leu Thr
1               5

<210> SEQ ID NO 37
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 37

Gln Gln Asn Met Gln Leu Pro Leu Thr
1               5

<210> SEQ ID NO 38
<211> LENGTH: 6
<212> TYPE: PRT
<213> ORGANISM: Artificial Sequence
<220> FEATURE:
<223> OTHER INFORMATION: The sequence is synthesized

```
<400> SEQUENCE: 38

Ser Asn Asn Gly Met His
1               5

<210> SEQ ID NO 39
<211> LENGTH: 6
<212> TYPE: PRT
<213> ORGANISM: Artificial Sequence
<220> FEATURE:
<223> OTHER INFORMATION: The sequence is synthesized

<400> SEQUENCE: 39

Ser Asn Tyr Gly Met His
1               5

<210> SEQ ID NO 40
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 40

Val Ile Trp Tyr Asp Gly Ser Lys Lys
1               5

<210> SEQ ID NO 41
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 41

Val Ile Trp Tyr Asp Ser Ser Arg Lys
1               5

<210> SEQ ID NO 42
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 42

Val Ile Trp Tyr Asp Ser Thr Lys Lys
1               5

<210> SEQ ID NO 43
<211> LENGTH: 13
<212> TYPE: PRT
<213> ORGANISM: Artificial Sequence
<220> FEATURE:
<223> OTHER INFORMATION: The sequence is synthesized

<400> SEQUENCE: 43

Thr Ala Val Tyr Tyr Cys Ala Thr Asn Asn Asp Tyr Trp
1               5                   10

<210> SEQ ID NO 44
<211> LENGTH: 13
<212> TYPE: PRT
<213> ORGANISM: Artificial Sequence
<220> FEATURE:
<223> OTHER INFORMATION: The sequence is synthesized

<400> SEQUENCE: 44
```

Thr Ala Val Tyr Tyr Cys Ala Thr Asn Thr Asp Tyr Trp
1               5                   10

<210> SEQ ID NO 45
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 45
gatatccaga tgacccagag c                                        21

<210> SEQ ID NO 46
<211> LENGTH: 32
<212> TYPE: DNA
<213> ORGANISM: Artificial Sequence
<220> FEATURE:
<223> OTHER INFORMATION: The sequence is synthesized

<400> SEQUENCE: 46
ctaagcggcc gctttgatct ccactttggt gc                            32

<210> SEQ ID NO 47
<211> LENGTH: 34
<212> TYPE: DNA
<213> ORGANISM: Artificial Sequence
<220> FEATURE:
<223> OTHER INFORMATION: The sequence is synthesized

<400> SEQUENCE: 47
cataccatgg cccaggtgca gctggtggag tctg                          34

<210> SEQ ID NO 48
<211> LENGTH: 33
<212> TYPE: DNA
<213> ORGANISM: Artificial Sequence
<220> FEATURE:
<223> OTHER INFORMATION: The sequence is synthesized

<400> SEQUENCE: 48
gctctgggtc atctggatat cggatccacc acc                           33

<210> SEQ ID NO 49
<211> LENGTH: 34
<212> TYPE: DNA
<213> ORGANISM: Artificial Sequence
<220> FEATURE:
<223> OTHER INFORMATION: The sequence is synthesized

<400> SEQUENCE: 49
cataccatgg cccaggtgca gctggtggag tctg                          34

<210> SEQ ID NO 50
<211> LENGTH: 27
<212> TYPE: DNA
<213> ORGANISM: Artificial Sequence
<220> FEATURE:
<223> OTHER INFORMATION: The sequence is synthesized

<400> SEQUENCE: 50
tgaggagacg gtgaccaggg tgccctg                                  27

<210> SEQ ID NO 51
<211> LENGTH: 33

-continued

<212> TYPE: DNA
<213> ORGANISM: Artificial Sequence
<220> FEATURE:
<223> OTHER INFORMATION: The sequence is synthesized

<400> SEQUENCE: 51
ctggtcaccg tctcctcagg tggtggtggt agc                                33

<210> SEQ ID NO 52
<211> LENGTH: 32
<212> TYPE: DNA
<213> ORGANISM: Artificial Sequence
<220> FEATURE:
<223> OTHER INFORMATION: The sequence is synthesized

<400> SEQUENCE: 52
ctaagcggcc gctttgatct ccactttggt gc                                 32

<210> SEQ ID NO 53
<211> LENGTH: 440
<212> TYPE: PRT
<213> ORGANISM: Artificial Sequence
<220> FEATURE:
<223> OTHER INFORMATION: It is synthesized

<400> SEQUENCE: 53

```
Gln Val Gln Leu Val Glu Ser Gly Gly Gly Val Val Gln Pro Gly Arg
  1               5                  10                  15

Ser Leu Arg Leu Asp Cys Lys Ala Ser Gly Ile Thr Phe Ser Asn Asn
             20                  25                  30

Gly Met His Trp Val Arg Gln Ala Pro Gly Lys Gly Leu Glu Trp Val
         35                  40                  45

Ala Val Ile Trp Tyr Asp Ser Thr Lys Lys Tyr Tyr Ala Asp Ser Val
     50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Thr Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255
```

```
Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 54
<211> LENGTH: 214
<212> TYPE: PRT
<213> ORGANISM: Artificial Sequence
<220> FEATURE:
<223> OTHER INFORMATION: It is synthesized

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile His Ser Tyr
            20                  25                  30

Leu Asp Trp Tyr Gln Gln Lys Pro Gly Lys Ala Pro Lys Leu Leu Ile
        35                  40                  45

Tyr Glu Ala Ser Thr Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Lys Leu Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 214
<212> TYPE: PRT
<213> ORGANISM: Artificial Sequence
<220> FEATURE:
<223> OTHER INFORMATION: It is synthesized

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Ser Asn Trp
            20                  25                  30

Leu Asp Trp Tyr Gln Gln Lys Pro Gly Lys Ala Pro Lys Leu Leu Ile
        35                  40                  45

Tyr Asp Ala Ser Asn Arg Ala Thr Gly Val Pro Ser Arg Phe Ser Gly
 50                 55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg His Ile Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 56
<211> LENGTH: 214
<212> TYPE: PRT
<213> ORGANISM: Artificial Sequence
<220> FEATURE:
<223> OTHER INFORMATION: It is synthesized

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile His Asn Tyr
            20                  25                  30

Leu Asp Trp Tyr Gln Gln Lys Pro Gly Lys Ala Pro Lys Leu Leu Ile
        35                  40                  45
```

```
Tyr Asn Ala Ser Thr Arg Ala Thr Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Glu Leu His Leu Pro Leu
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 57
<211> LENGTH: 214
<212> TYPE: PRT
<213> ORGANISM: Artificial Sequence
<220> FEATURE:
<223> OTHER INFORMATION: It is synthesized

<400> SEQUENCE: 57

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Asn Asn Trp
                 20                  25                  30

Leu Asp Trp Tyr Gln Gln Lys Pro Gly Lys Ala Pro Lys Leu Leu Ile
             35                  40                  45

Tyr Asp Ala Ser Thr Leu Ala Thr Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn Val Asn Leu Pro Leu
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 214
<212> TYPE: PRT
<213> ORGANISM: Artificial Sequence
<220> FEATURE:
<223> OTHER INFORMATION: It is synthesized

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Arg Asn Tyr
            20                  25                  30

Leu Asp Trp Tyr Gln Gln Lys Pro Gly Lys Ala Pro Lys Leu Leu Ile
        35                  40                  45

Tyr Gly Ala Ser Thr Arg Ala Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Asp Leu Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 214
<212> TYPE: PRT
<213> ORGANISM: Artificial Sequence
<220> FEATURE:
<223> OTHER INFORMATION: It is synthesized

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Trp
            20                  25                  30

Leu Asp Trp Tyr Gln Gln Lys Pro Gly Lys Ala Pro Lys Leu Leu Ile
        35                  40                  45

Tyr Asp Ala Ser Thr Arg Ala Thr Gly Val Pro Ser Arg Phe Ser Gly
```

```
            50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Arg Leu Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 60
<211> LENGTH: 214
<212> TYPE: PRT
<213> ORGANISM: Artificial Sequence
<220> FEATURE:
<223> OTHER INFORMATION: It synthesized

<400> SEQUENCE: 60

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Asn Tyr
            20                  25                  30

Leu Asp Trp Tyr Gln Gln Lys Pro Gly Lys Ala Pro Lys Leu Leu Ile
        35                  40                  45

Tyr Asp Ala Ser Thr Arg Ala Thr Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn Met Gln Leu Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
            195                 200                 205

Phe Asn Arg Gly Glu Cys
    210

<210> SEQ ID NO 61
<211> LENGTH: 440
<212> TYPE: PRT
<213> ORGANISM: Artificial Sequence
<220> FEATURE:
<223> OTHER INFORMATION: It is synthesized

<400> SEQUENCE: 61

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Ser Ser Arg Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
```

```
                340             345             350
Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
        420                 425                 430

Ser Leu Ser Leu Ser Leu Gly Lys
            435                 440

<210> SEQ ID NO 62
<211> LENGTH: 440
<212> TYPE: PRT
<213> ORGANISM: Artificial Sequence
<220> FEATURE:
<223> OTHER INFORMATION: It is synthesized

<400> SEQUENCE: 62

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Asn
            20                  25                  30

Gly Met His Trp Val Arg Gln Ala Pro Gly Lys Gly Leu Glu Trp Val
        35                  40                  45

Ala Val Ile Trp Tyr Asp Ser Ser Arg Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Thr Asn Asn Asp Tyr Trp Gly Gln Gly Thr Leu Val Thr Val Ser
        100                 105                 110

Ser Ala Ser Thr Lys Gly Pro Ser Val Phe Pro Leu Ala Pro Cys Ser
    115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
            145                 150                 155                 160

Ser Gly Val His Thr Phe Pro Ala Val Leu Gln Ser Ser Gly Leu Tyr
        165                 170                 175

Ser Leu Ser Ser Val Val Thr Val Pro Ser Ser Ser Leu Gly Thr Lys
    180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
        210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
```

```
                    260                 265                 270
Asp Gly Val Glu Val His Asn Ala Lys Thr Lys Pro Arg Glu Glu Gln
                275                 280                 285

Phe Asn Ser Thr Tyr Arg Val Ser Val Leu Thr Val Leu His Gln
            290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 63
<211> LENGTH: 440
<212> TYPE: PRT
<213> ORGANISM: Artificial Sequence
<220> FEATURE:
<223> OTHER INFORMATION: It is synthesized

<400> SEQUENCE: 63

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
```

```
                    180                  185                  190
Thr Tyr Thr Cys Asn Val Asp His Lys Pro Ser Asn Thr Lys Val Asp
                195                  200                  205
Lys Arg Val Glu Ser Lys Tyr Gly Pro Pro Cys Pro Pro Cys Pro Ala
            210                  215                  220
Pro Glu Phe Leu Gly Gly Pro Ser Val Phe Leu Phe Pro Pro Lys Pro
225                  230                  235                  240
Lys Asp Thr Leu Met Ile Ser Arg Thr Pro Glu Val Thr Cys Val Val
                245                  250                  255
Val Asp Val Ser Gln Glu Asp Pro Glu Val Gln Phe Asn Trp Tyr Val
                260                  265                  270
Asp Gly Val Glu Val His Asn Ala Lys Thr Lys Pro Arg Glu Glu Gln
            275                  280                  285
Phe Asn Ser Thr Tyr Arg Val Val Ser Val Leu Thr Val Leu His Gln
        290                  295                  300
Asp Trp Leu Asn Gly Lys Glu Tyr Lys Cys Lys Val Ser Asn Lys Gly
305                  310                  315                  320
Leu Pro Ser Ser Ile Glu Lys Thr Ile Ser Lys Ala Lys Gly Gln Pro
                325                  330                  335
Arg Glu Pro Gln Val Tyr Thr Leu Pro Pro Ser Gln Glu Glu Met Thr
            340                  345                  350
Lys Asn Gln Val Ser Leu Thr Cys Leu Val Lys Gly Phe Tyr Pro Ser
        355                  360                  365
Asp Ile Ala Val Glu Trp Glu Ser Asn Gly Gln Pro Glu Asn Asn Tyr
    370                  375                  380
Lys Thr Thr Pro Pro Val Leu Asp Ser Asp Gly Ser Phe Phe Leu Tyr
385                  390                  395                  400
Ser Arg Leu Thr Val Asp Lys Ser Arg Trp Gln Glu Gly Asn Val Phe
                405                  410                  415
Ser Cys Ser Val Met His Glu Ala Leu His Asn His Tyr Thr Gln Lys
            420                  425                  430
Ser Leu Ser Leu Ser Leu Gly Lys
        435                  440

<210> SEQ ID NO 64
<211> LENGTH: 1323
<212> TYPE: DNA
<213> ORGANISM: Artificial Sequence
<220> FEATURE:
<223> OTHER INFORMATION: It is synthesized

<400> SEQUENCE: 64
caggtgcagc tggtggagtc tgggggaggc gtggtccagc ctggggaggtc cctgagactc    60 gattgtaagg cgtctggaat caccttcagt aacaacggta tgcactgggt ccgccaggct   120
ccaggcaagg ggctggagtg ggtggcagtt atatggtacg atagtactaa aaagtactat   180
gcagactccg tgaagggccg attcaccatc tccagagaca attccaagaa cacgctgttt   240
ctgcaaatga acagcctgag agccgaggac acggctgtgt attactgtgc cactaacacc   300
gattactggg gccagggcac cctggtcacc gtgtcctccg cctccaccaa gggcccttcc   360
gtgttccctc tggccccttg ctcccgctcc acctccgagt ccaccgccgc cctgggctgc   420
ctggtgaagg actacttccc tgagcctgtg accgtgtcct ggaactccgg cgccctgacc   480
tccggcgtgc acaccttccc tgccgtgctg cagtcctccg gcctgtactc cctgtcctcc   540
gtggtgaccg tgccttcctc ctcccctgggc accaagacct acacctgcaa cgtggaccac   600
```

```
aagccttcca acaccaaggt ggacaagcgc gtggagtcca agtacggccc tccttgccct      660
ccttgccctg cccctgagtt cctgggcggc ccttccgtgt tcctgttccc tcctaagcct      720
aaggacaccc tgatgatctc ccgcacccct gaggtgacct gcgtggtggt ggacgtgtcc      780
caggaggacc ctgaggtgca gttcaactgg tacgtggacg gcgtggaggt gcacaacgcc      840
aagaccaagc ctcgcgagga gcagttcaac tccacctacc gcgtggtgtc cgtgctgacc      900
gtgctgcacc aggactggct gaacggcaag gagtacaagt gcaaggtgtc caacaagggc      960 ctgcccttcct ccatcgagaa gaccatctcc aaggccaagg ccagcctcg cgagcctcag     1020 gtgtacaccc tgcctccttc ccaggaggag atgaccaaga accaggtgtc cctgacctgc     1080
ctggtgaagg gcttctaccc cttccgacatc gccgtggagt gggagtccaa cggccagcct     1140
gagaacaact acaagaccac ccctcctgtg ctggactccg acggctcctt cttcctgtac     1200
tcccgcctga ccgtggacaa gtcccgctgg caggagggca acgtgttctc ctgctccgtg     1260
atgcacgagg ccctgcacaa ccactacacc cagaagtccc tgtccctgtc cctgggcaag     1320
tag                                                                   1323

<210> SEQ ID NO 65
<211> LENGTH: 642
<212> TYPE: DNA
<213> ORGANISM: Artificial Sequence
<220> FEATURE:
<223> OTHER INFORMATION: It is synthesized.

<400> SEQUENCE: 65
gatatccaga tgacccagag cccgagcagc ctgagcgcga gcgtgggtga tcgcgtgacc       60
attacctgcc gcgcgagcca gaatatccat agctacctgg attggtatca gcagaaaccg      120
ggtaaagcgc cgaaactgtt aatttatgag gccagcaccc gggcgtctgg cgtgccgtcg      180
cgttttagcg gctcgggttc gggcaccgat tttaccctga ccatctcgag cttgcagccg      240
gaggacttcg ccacctacta ttgccagcaa gcgctgaagc tgccaatcac cttcggtcag      300
ggcaccaaag tggagatcaa acgtacggtg gcggcgccat ctgtcttcat cttcccgcca      360
tctgatgagc agttgaaatc tggtaccgct agcgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                         642

<210> SEQ ID NO 66
<211> LENGTH: 642
<212> TYPE: DNA
<213> ORGANISM: Artificial Sequence
<220> FEATURE:
<223> OTHER INFORMATION: It is synthesized.

<400> SEQUENCE: 66
gatatccaga tgacccagag cccgagcagc ctgagcgcga gcgtgggtga tcgcgtgacc       60
attacctgcc gcgcgagcca gaatgtcagt aactggctgg attggtatca gcagaaaccg      120
ggtaaagcgc cgaaactgtt aatttatgat gccagcaacc gggcgactgg cgtgccgtcg      180
cgttttagcg gctcgggttc gggcaccgat tttaccctga ccatctcgag cttgcagccg      240
gaggacttcg ccacctacta ttgccagcaa tcgaggcaca tcccactcac cttcggtcag      300
```

| | |
|---|---|
| ggcaccaaag tggagatcaa acgtacggtg gcggcgccat ctgtcttcat cttcccgcca | 360 |
| tctgatgagc agttgaaatc tggtaccgct agcgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 67
<211> LENGTH: 642
<212> TYPE: DNA
<213> ORGANISM: Artificial Sequence
<220> FEATURE:
<223> OTHER INFORMATION: It is synthesized.

<400> SEQUENCE: 67

| | |
|---|---|
| gatatccaga tgacccagag cccgagcagc ctgagcgcga gcgtgggtga tcgcgtgacc | 60 |
| attacctgcc gcgcgagcca gagtatccat aactacctgg attggtatca gcagaaaccg | 120 |
| ggtaaagcgc cgaaactgtt aatttataat gccagcaccc gggcgactgg cgtgccgtcg | 180 |
| cgttttagcg gctcgggttc gggcaccgat tttaccctga ccatctcgag cttgcagccg | 240 |
| gaggacttcg ccacctacta ttgccagcaa gagctccacc tgccactcac cttcggtcag | 300 |
| ggcaccaaag tggagatcaa acgtacggtg gcggcgccat ctgtcttcat cttcccgcca | 360 |
| tctgatgagc agttgaaatc tggtaccgct agcgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 68
<211> LENGTH: 642
<212> TYPE: DNA
<213> ORGANISM: Artificial Sequence
<220> FEATURE:
<223> OTHER INFORMATION: It is synthesized.

<400> SEQUENCE: 68

| | |
|---|---|
| gatatccaga tgacccagag cccgagcagc ctgagcgcga gcgtgggtga tcgcgtgacc | 60 |
| attacctgcc gcgcgagcca ggatatcaat aactggctgg attggtatca gcagaaaccg | 120 |
| ggtaaagcgc cgaaactgtt aatttatgat gccagcaccc tggcgactgg cgtgccgtcg | 180 |
| cgttttagcg gctcgggttc gggcaccgat tttaccctga ccatctcgag cttgcagccg | 240 |
| gaggacttcg ccacctacta ttgccagcaa aacgtgaacc tgccactgac cttcggtcag | 300 |
| ggcaccaaag tggagatcaa acgtacggtg gcggcgccat ctgtcttcat cttcccgcca | 360 |
| tctgatgagc agttgaaatc tggtaccgct agcgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 69
<211> LENGTH: 642

<212> TYPE: DNA
<213> ORGANISM: Artificial Sequence
<220> FEATURE:
<223> OTHER INFORMATION: It is synthesized

<400> SEQUENCE: 69

```
gatatccaga tgacccagag cccgagcagc ctgagcgcga gcgtgggtga tcgcgtgacc      60
attacctgcc gcgcgagcca ggatgtccgt aactacctgg attggtatca gcagaaaccg     120
ggtaaagcgc cgaaactgtt aatttatggg gccagcaccc gggcgactgg cgtgccgtcg     180
cgttttagcg gctcgggttc gggcaccgat tttaccctga ccatctcgag cttgcagccg     240
gaggacttcg ccacctacta ttgccagcaa gacatcgatc tgccattgac cttcggtcag     300
ggcaccaaag tggagatcaa acgtacggtg gcggcgccat ctgtcttcat cttcccgcca     360
tctgatgagc agttgaaatc tggtaccgct agcgttgtgt gcctgctgaa taacttctat     420
cccagagagg ccaaagtaca gtggaaggtg ataacgccc tccaatcggg taactcccag      480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 70
<211> LENGTH: 642
<212> TYPE: DNA
<213> ORGANISM: Artificial Sequence
<220> FEATURE:
<223> OTHER INFORMATION: It is synthesized.

<400> SEQUENCE: 70

```
gatatccaga tgacccagag cccgagcagc ctgagcgcga gcgtgggtga tcgcgtgacc      60
attacctgcc gcgcgagcca gggtatcaat agctggctgg attggtatca gcagaaaccg     120
ggtaaagcgc cgaaactgtt aatttatgat gccagcaccc gggcgactgg cgtgccgtcg     180
cgttttagcg gctcgggttc gggcaccgat tttaccctga ccatctcgag cttgcagccg     240
gaggacttcg ccacctacta ttgccagcaa agctaccggc tcccactcac cttcggtcag     300
ggcaccaaag tggagatcaa acgtacggtg gcggcgccat ctgtcttcat cttcccgcca     360
tctgatgagc agttgaaatc tggtaccgct agcgttgtgt gcctgctgaa taacttctat     420
cccagagagg ccaaagtaca gtggaaggtg ataacgccc tccaatcggg taactcccag      480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 71
<211> LENGTH: 642
<212> TYPE: DNA
<213> ORGANISM: Artificial Sequence
<220> FEATURE:
<223> OTHER INFORMATION: It is synthesized

<400> SEQUENCE: 71

```
gatatccaga tgacccagag cccgagcagc ctgagcgcga gcgtgggtga tcgcgtgacc      60
attacctgcc gcgcgagcca gagtgtcagt aactacctgg attggtatca gcagaaaccg     120
ggtaaagcgc cgaaactgtt aatttatgat gccagcaccc gggcgactgg cgtgccgtcg     180
cgttttagcg gctcgggttc gggcaccgat tttaccctga ccatctcgag cttgcagccg     240
```

```
gaggacttcg ccacctacta ttgccagcaa acatgcagc tcccactcac cttcggtcag      300
ggcaccaaag tggagatcaa acgtacggtg cggcgccat ctgtcttcat cttcccgcca      360
tctgatgagc agttgaaatc tggtaccgct agcgttgtgt gcctgctgaa taacttctat     420
cccagagagg ccaaagtaca gtggaaggtg ataacgccc tccaatcggg taactcccag      480
gagagtgtca cagagcagga cagcaaggac agcacctaca gcctcagcag caccctgacg     540
ctgagcaaag cagactacga gaaacacaaa gtctacgcct cgaagtcac ccatcagggc      600 ctgagctcgc ccgtcacaaa gagcttcaac aggggagagt gt                       642
```

<210> SEQ ID NO 72
<211> LENGTH: 1323
<212> TYPE: DNA
<213> ORGANISM: Artificial Sequence
<220> FEATURE:
<223> OTHER INFORMATION: It is synthesized.

<400> SEQUENCE: 72

```
caggtgcagc tggtggagtc tgggggaggc gtggtccagc ctggggaggtc cctgagactc      60 gattgtaagg cgtctggaat caccttcagt aactacggta tgcactgggt ccgccaggct     120
ccaggcaagg ggctggagtg ggtggcagtt atatggtacg atagtagtag aaagtactat     180
gcagactccg tgaagggccg attcaccatc tccagagaca attccaagaa cacgctgttt     240
ctgcaaatga acagcctgag agccgaggac acggctgtgt attactgtgc cactaacaac     300
gattactggg gccagggcac cctggtcacc gtgtcctccg cctccaccaa gggcccttcc     360
gtgttccctc tggccccttg ctcccgctcc acctccgagt ccaccgccgc cctgggctgc     420
ctggtgaagg actacttccc tgagcctgtg accgtgtcct ggaactccgg cgccctgacc     480
tccggcgtgc acaccttccc tgccgtgctg cagtcctccg gcctgtactc cctgtcctcc     540
gtggtgaccg tgccttcctc ctccctgggc accaagacct acacctgcaa cgtggaccac     600
aagccttcca caccaaggt ggacaagcgc gtggagtcca agtacggccc tccttgccct      660
ccttgccctg cccctgagtt cctgggcggc ccttccgtgt tcctgttccc tcctaagcct     720
aaggacaccc tgatgatctc ccgcacccct gaggtgacct gcgtggtggt ggacgtgtcc     780
caggaggacc ctgaggtgca gttcaactgg tacgtggacg gcgtggaggt gcacaacgcc     840
aagaccaagc ctcgcgagga gcagttcaac tccacctacc gcgtggtgtc cgtgctgacc     900
gtgctgcacc aggactggct gaacggcaag gagtacaagt gcaaggtgtc caacaagggc     960 ctgcccttcct ccatcgagaa gaccatctcc aaggccaagg ccagcctcg cgagcctcag    1020 gtgtacacccc tgcctccttc ccaggaggag atgaccaaga accaggtgtc cctgacctgc    1080
ctggtgaagg gcttctaccc ttccgacatc gccgtggagt gggagtccaa cggcagcct     1140 gagaacaact acaagaccac ccctcctgtg ctggactccg acggctcctt cttcctgtac    1200
tcccgcctga ccgtggacaa gtcccgcctgg caggagggca acgtgttctc ctgctccgtg    1260
atgcacgagg ccctgcacaa ccactacacc cagaagtccc tgtccctgtc cctgggcaag    1320
tag                                                                 1323
```

<210> SEQ ID NO 73
<211> LENGTH: 1323
<212> TYPE: DNA
<213> ORGANISM: Artificial Sequence
<220> FEATURE:
<223> OTHER INFORMATION: It is synthesized.

<400> SEQUENCE: 73

```
caggtgcagc tggtggagtc tgggggaggc gtggtccagc ctgggaggtc cctgagactc      60
gattgtaagg cgtctggaat caccttcagt aactacggta tgcactgggt ccgccaggct     120
ccaggcaagg ggctggagtg ggtggcagtt atatggtacg atagtagtag aaagtactat     180
gcagactccg tgaagggccg attcaccatc tccagagaca attccaagaa cacgctgttt     240
ctgcaaatga acagcctgag agccgaggac acggctgtgt attactgtgc cactaacaac     300
gattactggg gccagggcac cctggtcacc gtgtcctccg cctccaccaa gggcccttcc     360
gtgttccctc tggccccttg ctcccgctcc acctccgagt ccaccgccgc cctgggctgc     420
ctggtgaagg actacttccc tgagcctgtg accgtgtcct ggaactccgg cgccctgacc     480
tccggcgtgc acaccttccc tgccgtgctg cagtcctccg gcctgtactc cctgtcctcc     540
gtggtgaccg tgccttcctc ctccctgggc accaagacct acacctgcaa cgtggaccac     600
aagccttcca acaccaaggt ggacaagcgc gtggagtcca agtacggccc tccttgccct     660
ccttgccctg cccctgagtt cctgggcggc ccttccgtgt tcctgttccc tcctaagcct     720
aaggacaccc tgatgatctc ccgcaccect gaggtgacct gcgtggtggt ggacgtgtcc     780
caggaggacc ctgaggtgca gttcaactgg tacgtggacg gcgtggaggt gcacaacgcc     840
aagaccaagc ctcgcgagga gcagttcaac tccacctacc gcgtggtgtc cgtgctgacc     900
gtgctgcacc aggactggct gaacggcaag gagtacaagt gcaaggtgtc caacaagggc     960
ctgcctccct ccatcgagaa gaccatctcc aaggccaagg gccagcctcg cgagcctcag    1020
gtgtacaccc tgcctccttc ccaggaggag atgaccaaga accaggtgtc cctgacctgc    1080
ctggtgaagg gcttctaccc ttccgacatc gccgtggagt gggagtccaa cggccagcct    1140
gagaacaact acaagaccac ccctcctgtg ctggactccg acggctcctt cttcctgtac    1200
tcccgcctga ccgtggacaa gtcccgctgg caggagggca cgtgttctc ctgctccgtg    1260 atgcacgagg ccctgcacaa ccactacacc cagaagtccc tgtccctgtc cctgggcaag    1320
tag                                                                  1323
```

<210> SEQ ID NO 74
<211> LENGTH: 1323
<212> TYPE: DNA
<213> ORGANISM: Artificial Sequence
<220> FEATURE:
<223> OTHER INFORMATION: It is synthesized.

<400> SEQUENCE: 74

```
caggtgcagc tggtggagtc tgggggaggc gtggtccagc ctgggaggtc cctgagactc      60
gattgtaagg cgtctggaat caccttcagt aacaacggta tgcactgggt ccgccaggct     120
ccaggcaagg ggctggagtg ggtggcagtt atatggtacg atagtagtag aaagtactat     180
gcagactccg tgaagggccg attcaccatc tccagagaca attccaagaa cacgctgttt     240
ctgcaaatga acagcctgag agccgaggac acggctgtgt attactgtgc cactaacaac     300
gattactggg gccagggcac cctggtcacc gtgtcctccg cctccaccaa gggcccttcc     360
gtgttccctc tggccccttg ctcccgctcc acctccgagt ccaccgccgc cctgggctgc     420
ctggtgaagg actacttccc tgagcctgtg accgtgtcct ggaactccgg cgccctgacc     480
tccggcgtgc acaccttccc tgccgtgctg cagtcctccg gcctgtactc cctgtcctcc     540
gtggtgaccg tgccttcctc ctccctgggc accaagacct acacctgcaa cgtggaccac     600
aagccttcca acaccaaggt ggacaagcgc gtggagtcca agtacggccc tccttgccct     660
```

```
ccttgccctg cccctgagtt cctgggcggc ccttccgtgt tcctgttccc tcctaagcct    720
aaggacaccc tgatgatctc ccgcacccct gaggtgacct gcgtggtggt ggacgtgtcc    780
caggaggacc ctgaggtgca gttcaactgg tacgtggacg gcgtggaggt gcacaacgcc    840
aagaccaagc ctcgcgagga gcagttcaac tccacctacc gcgtggtgtc cgtgctgacc    900
gtgctgcacc aggactggct gaacggcaag gagtacaagt gcaaggtgtc caacaagggc    960
ctgccttcct ccatcgagaa gaccatctcc aaggccaagg gccagcctcg cgagcctcag   1020
gtgtacaccc tgcctccttc ccaggaggag atgaccaaga accaggtgtc cctgacctgc   1080
ctggtgaagg gcttctaccc ttccgacatc gccgtggagt gggagtccaa cggccagcct   1140
gagaacaact acaagaccac ccctcctgtg ctggactccg acggctcctt cttcctgtac   1200
tcccgcctga ccgtggacaa gtcccgctgg caggagggca acgtgttctc ctgctccgtg   1260
atgcacgagg ccctgcacaa ccactacacc cagaagtccc tgtccctgtc cctgggcaag   1320
tag                                                                 1323
```